United States Patent [19]
Vaccaro et al.

[11] Patent Number: 6,100,279
[45] Date of Patent: Aug. 8, 2000

[54] IMIDAZOYLALKYL SUBSTITUTED WITH A FIVE, SIX OR SEVEN MEMBERED HETEROCYCLIC RING CONTAINING ONE NITROGEN ATOM

[75] Inventors: Wayne D. Vaccaro, Yardley, Pa.; Ronald L. Wolin, Bedminster, N.J.; Daniel M. Solomon, Edison, N.J.; Robert G. Aslanian, Rockaway, N.J.; John J. Piwinski, Clinton Township, N.J.; Stuart B. Rosenblum, West Orange, N.J.

[73] Assignee: Schering Corporation, Kenilworth, N.J.

[21] Appl. No.: 09/185,973

[22] Filed: Nov. 5, 1998

Related U.S. Application Data

[60] Provisional application No. 60/064,958, Nov. 7, 1997.
[51] Int. Cl.[7] .................. A61K 31/445; C07D 401/06
[52] U.S. Cl. .................. 514/326; 514/212; 514/397; 540/603; 546/210; 548/314.7
[58] Field of Search .................. 514/212, 326, 514/397; 540/603; 546/210; 548/314.7

[56] References Cited

U.S. PATENT DOCUMENTS

| | | | |
|---|---|---|---|
| 5,463,074 | 10/1995 | Shih et al. | 548/314.7 |
| 5,559,113 | 9/1996 | Schwartz et al. | 514/252 |
| 5,578,616 | 11/1996 | Aslanian et al. | 514/341 |
| 5,708,171 | 1/1998 | Schwartz et al. | 544/324 |
| 5,807,872 | 9/1998 | Shih et al. | 514/326 |
| 5,869,479 | 2/1999 | Kreutner et al. | 514/212 |

FOREIGN PATENT DOCUMENTS

| | | |
|---|---|---|
| WO 93 12107 | 6/1993 | WIPO . |
| WO 93 12108 | 6/1993 | WIPO . |
| WO 93 14070 | 7/1993 | WIPO . |
| 95/06037 | 3/1995 | WIPO . |
| WO 95 06037 | 3/1995 | WIPO . |
| WO 95 14007 | 5/1995 | WIPO . |
| WO 96 29315 | 9/1996 | WIPO . |
| WO 98 06394 | 2/1998 | WIPO . |

OTHER PUBLICATIONS

Leurs et al. "The histamine H3 receptor . . . " progree in Drug Res. V. 39, p. 139, 1992.
Schunack et al. "Benzhydryl ethers possessing combined histamine H3/H1 receptor antagonist activity" BIOSIS 10782164, 1996.
Snyman et al. "Influence of histamine receptor antagonists . . . " MEDLINE 07777637, 1993.

*Primary Examiner*—Ceila Chang
*Attorney, Agent, or Firm*—Henry C. Jeanette

[57] ABSTRACT

Disclosed are compounds of Formula I

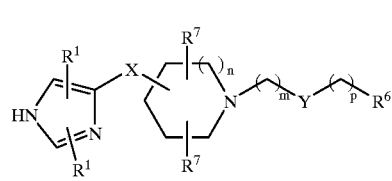

(I)

or pharmaceutically acceptable salts or solvates thereof. Also disclosed are pharmaceutical compositions comprising a pharmaceutically acceptable carrier and an effective amount of a Compound of Formula I. Further disclosed is a method of treating allergy (for example asthma), inflammation, hypotension, raised intraocular pressure (such as glaucoma)—i.e., a method of lowering intraocular pressure, sleeping disorders, states of hyper and hypo motility and acidic secretion of the gastrointestinal tract, hypo and hyperactivity of the central nervous system (for example, agitation and depression) and other CNS disorders (such as Alzheimer's, schizophrenia, obesity and migraine) comprising administering an effective amount of a compound of Formula I to a patient in need of such treatment. Also disclosed are methods for treatment of upper airway allergic responses comprising administering a compound, or salt or solvate thereof, of formula I in combination or admixture with a histamine H, receptor antagonist.

23 Claims, No Drawings

IMIDAZOYLALKYL SUBSTITUTED WITH A FIVE, SIX OR SEVEN MEMBERED HETEROCYCLIC RING CONTAINING ONE NITROGEN ATOM

REFERENCE TO RELATED APPLICATIONS

This application claims the benefit of U.S. Provisional Application Ser. No. 60/064,958 filed Nov. 7, 1997.

BACKGROUND $H_3$ receptor sites are known and are of current interest to those skilled in the art—for example, see: West, Jr. et al., "Biexponential Kinetics of (R)-α-[$^3$H]Methylhistamine Binding to the Rat Brain $H_3$ Histamine Receptor", Journal of Neurochemistry, Vol. 55, No. 5, pp. 1612–1616, 1990; West, Jr. et al., "Identification of Two $H_3$-Histamine Receptor Subtypes", Molecular Pharmacology, 38:610–613; and Korte et al., "Characterization and Tissue Distribution of $H_3$ Histamine Receptors in Guinea Pigs by $N^\alpha$-Methylhistamine", Biochemical and Biophysical Research Communications, Vol. 168, No. 3, pp. 979–986.

Arrang et al. in U.S. Pat. No. 4,767, 778 (Issued Aug. 30, 1988) disclose a pharmaceutical composition containing a histamine derivative of the formula:

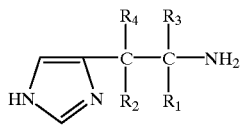

wherein each of $R_1$, $R_2$, and $R_4$, represents a hydrogen or a methyl, or R, and $R_2$ taken together represent a methylene, and $R_3$ is a hydrogen, a methyl or a carboxy, with the proviso that $R_1$, $R_2$, $R_3$, and $R_4$ are not simultaneously methyl groups. It is disclosed that the derivatives behave as complete agonists of the $H_3$ receptors in rat brain and produce a maximal inhibition of release identical to that induced by histamine (approximately 60%). It is also disclosed that the histamine derivatives powerfully inhibit the release and synthesis of histamine by very selectively stimulating the $H_3$ receptors. Consequently, according to Arrang et al., the derivatives are likely to decrease histaminergic transmission in the digestive tract and in the nervous, cardiovascular and immune systems. Arrang et al. disclose that the derivatives can be used in therapy as a drug having sedative effects, as a sleep regulator, anticonvulsant, regulator of hypothalmic-hypophyseal secretion, antidepressant, and modulator of cerebral circulation. According to Arrang et al., inhibition of the release of inflammation messengers in various allergic conditions (e.g., asthma) is expected to result from stimulation of the $H_3$ receptors of the lung. It is further disclosed that the inhibition of release of gastric histamine is likely to exert antisecretory and anti ulcerative effects. According to Arrang et al., modification of release of the messengers of immune responses is likely to modulate the latter responses.

Derwent abstract 86-273706/42 for EP 0 197 840 discloses imidazole derivatives of the formula:

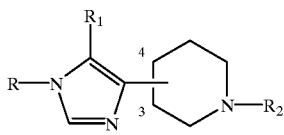

wherein $R_1$ is H, methyl or ethyl; R is H or $R_2$; and $R_2$ is 1-6C alkyl, piperonyl, 3-(benzimidazolon-1-yl)propyl, —CZ—NHR$_5$ or a group (i):

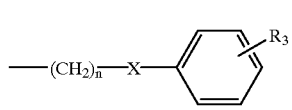

wherein n is 0–3; X is a bond, O, S, NH, CO, CH=CH or a group (ii):

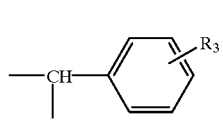

$R_3$ is H, methyl, halo, CN, CF$_3$ or COR$_4$; $R_4$ is 1-6C alkyl, 3-6C cycloalkyl or phenyl (optionally substituted by methyl or F); Z is O, S, NH, N-methyl or N—CN; and $R_5$ is 1-8C alkyl, 3-6C cycloalkyl (optionally substituted by phenyl), 3-6C cycloalkyl(1-3C)alkyl, phenyl (optionally substituted by methyl, halo or CF$_3$), phenyl(1-3C)alkyl, naphthyl, adamantyl or p-toluenesulphonyl. It is disclosed that these compounds are psychotropic agents. It is also disclosed that these compounds antagonize the histamine H3 receptors and increase the speed of cerebral histamine renewal.

Derwent abstract 90-184730/24 for U.S. Pat. No. 4,925, 851 discloses 2- or 4-(2-(1H-imidazol-1-yl)ethyl) piperidine compounds useful as antitumour agents for inhibiting lymphoma, sarcoma, myeloma and leukemia. The compounds have the formula:

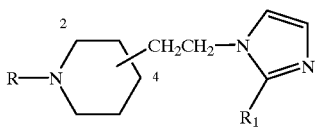

wherein R is —CH$_2$(CH$_2$)$_m$—Me, —CO—(CH$_2$)$_m$—Me or —CO—CMe$_2$—R$_2$; m is 2–18; $R_2$ is H or Me; $R_1$ is —(CH$_2$)$_n$—R$_3$; n is 0–13; $R_3$ is H, i-Pr or t-Bu; and the floating group is at the 2- or 4-position; with the proviso that (1) the sum of C atoms in $R_1$ does not exceed 13; and (2) the sum of C atoms in R and $R_1$ does not exceed 25.

WO 93/12107 published Jun. 24, 1993 discloses a compound of the formula:

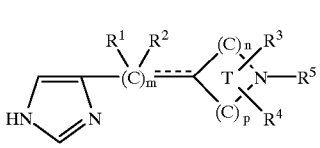

or a pharmaceutically acceptable salt or solvate thereof, wherein:

(A) m is an integer selected from the group consisting of: 1 and 2;
(B) n and p are integers and are each independently selected from the group consisting of: 0,1, 2, 3, and 4 such that the sum of n and p is 4 and T is a 6-membered ring;
C) $R^3$ and $R^4$ are each independently bound to the same or different carbon atom of ring T such that there is only one $R^3$ group and one $R^4$ group in ring T, and each $R^1$, $R^2$, $R^3$, and $R^4$ is independently selected from the group consisting of:
  (1) H;
  (2) $C_1$ to $C_6$ alkyl; and
  (3) —$(CH_2)_q$—$R^6$ wherein q is an integer of: 1 to 7, and $R^6$ is selected from the group consisting of: phenyl, substituted phenyl, —$OR^7$, —$C(O)OR^7$, —$C(O)R^7$, —$OC(O)R^7$, —$C(O)NR^7R^8$, CN and —$SR^7$ wherein $R^7$ and $R^8$ are as defined below, and wherein the substituents on said substituted phenyl are each independently selected from the group consisting of: —OH, —O—($C_1$ to $C_6$)alkyl, halogen, $C_1$ to $C_6$ alkyl, —$CF_3$, —CN, and —$NO_2$, and wherein said substituted phenyl contains from 1 to 3 substituents;
(D) $R^5$ is selected from the group consisting of:
  (1) H;
  (2) $C_1$ to $C_{20}$ alkyl;
  (3) $C_3$ to $C_6$ cycloalkyl;
  (4) —$C(O)OR^{7'}$; wherein $R^{7'}$ is the same as $R^7$ defined below except that $R^{7'}$ is not H;
  (5) —$C(O)R^7$;
  (6) —$C(O)NR^7R^8$;
  (7) allyl;
  (8) propargyl; and
  (9) —$(CH_2)_q$—$R^6$, wherein q and $R^6$ are as defined above, and when q is equal to 1, then $R^6$ is not OH or SH;
(E) $R^7$ and $R^8$ are each independently selected from the group consisting of: H, $C_1$ to $C_6$ alkyl, and $C_3$ to $C_6$ cycloalkyl;
(F) the dotted line (=) represents a double bond that is optionally present when m is 1, and n is not 0, and p is not 0, and when said double bond is present then $R^2$ is absent; and
(G) when m is 2, each $R^1$ is the same or different substituent for each m, and each $R^2$ is the same or different substituent for each m, and at least two of the substituents $R^1$ and/or $R^2$ are H.

These two latter documents claim the use of the compounds for treatment of allergy and other disorders.

EP 0 428 434 A2 as well as WO 96/29315 and WO 95/06037 describe a wide range of compounds and claim their use as $H_3$ receptor (ant)agonist. The above documents also include a comprehensive summary of the art dealing with this chemical field.

U.S. application Ser. No. 08/689951 filed Aug. 16, 1996 and U.S. application Ser. No. 08/909319 filed Aug. 14, 1997 disclose compositions for the treatment of the symptoms of allergic rhinitis using a combination of at least one histamine $H_1$ receptor antagonist and at least one histamine $H_3$ receptor antagonist.

In view of the art's interest in compounds which affect the $H_3$ receptors, novel compounds having antagonist activity on $H_3$ receptors would be a welcome contribution to the art. This invention provides just such a contribution by providing novel compounds having $H_3$ antagonist activity.

SUMMARY OF THE INVENTION

This invention relates to compounds of formula I

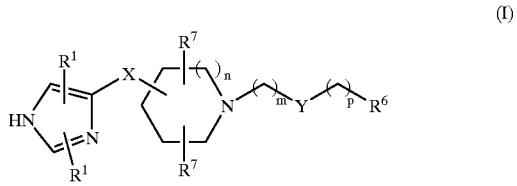

(I)

or pharmaceutically acceptable salts or solvates thereof, wherein:

X is a straight chain alkyl group having 1 to 7 carbon atoms or an alkene or alkyne group with 2 to 4 carbon atoms; wherein said alkyl or alkene groups are optionally substituted with up to two (i.e., 1 or 2) $R^7$ groups;

n is 0,1 or 2, m and p are 0 to 4;

when m is 0 to 4, Y represents —$SO_2$—; —CS—; —CO—; —$CONR^5$—; —$CO(CH_2)_wO$— (with w being 1 to 4); —COO—; —$CON(OR^5)$—; —$C(NR^5)NR^5$—; —$SO_2NR^5$— or —$CSNR^5$—;

when m is 2 to 4, Y represents all the groups above when m is 0 to 4 and, in addition, Y represents —$CHOR^5$—; —O—; —$NR^5CONR^5$—; —$NR^5CO$—; —$NR^5$—; —$OCONR^5$—; —$NR^5C(NR^5)NR^5$—; —$NR^5CSNR^5$; —$NR^5CS$— or —$NR^5SO_2$—; —$NR^5C(O)O$—; or —$CSNR^5$—;

each $R^5$ independently represents hydrogen, alkyl or benzyl;

$R^6$ represents aryl, heteroaryl, or a 3- to 7-membered heterocyclic group having one to three heteroatoms in the ring, wherein the heteroatoms are selected from N, S and O, and wherein said $R^6$ group is optionally substituted by one to three substituents as defined below;

when Y is —$SO_2$—, then $R^6$, in addition to the above groups, also represents alkyl having 1 to 7 carbon atoms or a group —$NR^{10}R^{11}$ wherein $R^{10}$ and $R^{11}$ are independently selected from H, alkyl or trihalomethyl;

each $R^1$ is independently hydrogen, alkyl or trihalomethyl;

each $R^7$ is independently selected from hydrogen, alkyl, trihalomethyl, phenyl or benzyl, , wherein said phenyl and benzyl are optionally substituted by one to three substituents independently selected from of alkyl, halogen, trihalomethyl, CN, $NO_2$, $OR^{10}$ or $NR^{10}R^{11}$, wherein $R^{10}$ and $R^{11}$ are as above defined.

This invention also provides pharmaceutical compositions comprising a pharmaceutically acceptable carrier and an effective amount of a compound (or a salt or solvate thereof) of Formula I.

This invention further provides a method of treating allergy, (for example asthma), inflammation, cardiovascular disease, hypotension, raised intraocular pressure (such as glaucoma)—i.e., a method of lowering intraocular pressure, sleeping disorders (e.g., hypersomnia, somnolence, narcolepsy and sleeplessness, such as insomnia), diseases of the GI tract, states of hyper and hypo motility and acidic secretion of the gastrointestinal tract, disturbances of the central nervous system, hypo and hyperactivity of the central nervous system (for example, agitation and depression) and other CNS disorders (such as Alzheimer's, schizophrenia, obesity and migraine) comprising administering an effective amount of a compound (or a salt or solvate thereof) of Formula I to a patient in need of such treatment.

This invention further provides a method for treating upper airway allergic responses by comprising administering an effective amount of a compound of Formula I (or a salt or solvate thereof) in combination or admixture with a suitable $H_1$ receptor antagonist.

DETAILED DESCRIPTION OF THE INVENTION

As used herein the following terms have the following meanings unless indicated otherwise:

alkyl—represents a straight or branched, saturated hydrocarbon chain having from 1 to 6 carbon atoms;

lower alkyl (including the alkyl portions of lower alkoxy)—represents a straight or branched, saturated hydrocarbon chain having from 1 to 6 carbon atoms, preferably from 1 to 4;

cycloalkyl—represents a saturated carbocyclic ring having from 3 to 6 carbon atoms, optionally substituted by 1 to 3 groups independently selected from the group consisting of lower alkyl, trihalomethyl and $NR^{10}R^{11}$, wherein $R^{10}$ and $R^{11}$ as defined above;

halogen (halo)—represents fluoro, chloro, bromo or iodo;

aryl—represents a carbocyclic group having from 6 to 14 carbon atoms and having at least one benzenoid ring, with all available substitutable aromatic carbon atoms of the carbocyclic group being intended as possible points of attachment, said carbocyclic group being optionally substituted with 1 to 3 groups, each independently selected from halo, alkyl, hydroxy, phenoxy, amino, loweralkylamino, diloweralkylamino, (e.g., $NR^{10}R^{11}$ wherein $R^{10}$ and $R^{11}$ are independently selected from hydrogen, lower alkyl or trihalomethyl), loweralkoxy, polyhaloloweralkoxy, (e.g., $OR^{10}$ wherein $R^{10}$ is as above defined) polyhaloloweralkyl (e.g., trihalomethyl), CN, or $NO_2$; preferred aryl groups include 1-naphthyl, 2-naphthyl and indanyl, and especially phenyl and substituted phenyl;

heterocyclic—represents saturated and unsaturated non-aromatic cyclic organic groups having at least one O, S and/or N atom interrupting a carbocyclic ring structure that consists of one ring or two fused rings, wherein each ring is 3 to 7 membered (e.g., 5-, 6- or 7-membered), which ring structure has from 2 to 8, preferably from 3 to 6 carbon atoms; e.g., 2- or 3-pyrrolidinyl, 2-, 3- or 4-piperidinyl, 2- or 3-piperazinyl, 2- or 3-morpholinyl, or 2- or 3-thiomorpholinyl; said heterocyclic group being optionally substituted by 1 to 3 groups independently selected from alkyl, trihalomethyl and $NR^{10}R^{11}$, wherein $R^{10}$ and $R^{11}$ are independently selected from hydrogen, alkyl or trihalomethyl, said substituents being bound to carbon atoms (substitutable carbon atoms) in the ring such that the total number of substituents in the ring is 1 to 3; and wherein said heterocyclic ring contains nitrogen atoms, said nitrogen atoms (i.e., the substitutable nitrogen atoms) being optionally substituted with lower alkyl (e.g., methyl), e.g., N-methylpyrrolidinyl;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc.; preferred heteroaryl groups are 2-, 3- and 4-pyridyl; said heteroaryl groups being optionally substituted with 1 to 3 groups, each optional substituent being independently selected from alkyl, halogen, trihalomethyl, CN, $NO_2$, $OR^{10}$ or $NR^{10}R^{11}$, wherein $R^{10}$ and $R^{11}$ are independently selected from hydrogen, alkyl or trihalomethyl, said substituents being bound to carbon atoms (substitutable carbon atoms) in the ring such that the total number of substituents in the ring is 1 to 3;

DMF—stands for N,N,-dimethylformamide;
SEM—stands for 2-(trimethylsilyl)ethoxymethyl;
THF—stands for tetrahydrofuran;
DMAP—stands for dimethylaminopyridine;
DIPA—stands for diisopropylamine;
DMSO—stands for dimethyl sulfoxide;
DBU—stands for diazabicycloundecene;
DBN—stands for diazabicyclononane;
LAH—stands for lithium aluminum hydride;
FAB—stands for fast atom bombardment;
CI—stands for chemical ionization;
EI—stands for electron impact;
HOBT—stands for 1-hydroxybenzotriazole;
EDCI—stands for 1-(3-dimethylaminopropyl)-3-ethylcarbodiimide hydrochloride;
LC/MS—stands for liquid chromatography/mass spectrometry;
TFA—stands for trifluroacetic acid;
Tr—stands for trityl; and
LRMS—stands for low resolution mass spectrometry.

Also, unless stated otherwise, the substituents for the various embodiments described below are as defined for Formula I.

Preferred compounds are represented by of formula II

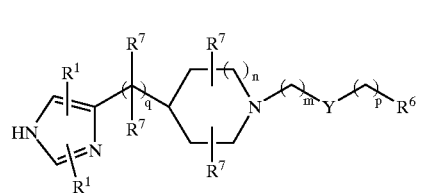

(II)

wherein q is 1 to 7, m is 0 to 4, n is 0 or 1, p is 0 to 4, Y is selected from —$SO_2$—, —$SO_2NH$—, —CONH—, —CO—, —C(NH)NH—, or —CO(CH$_2$)$_w$O—, or, when m is 2 to 4, Y. in addition to the groups above, also represents —NHCONH—, —O— or —NHC(NH)NH—; and w, $R^1$, $R^6$, and $R^7$ are as defined above.

Preferably $R^6$ is phenyl or substituted phenyl. Most preferred are compounds of formula II wherein (1) q is 1 to 4; (2) n is 0 or 1; (3) m is 0 to 4 (more preferably, 0 to 3, and even more preferably 0 to 2); (4) p is 0 to 2; (5) Y is —CONH—, —CO—, —$SO_2$—, —$CO(CH_2)_2O$— or —O— (when m is greater than or equal to 2, i.e., Y can also be —O— when m is 2 -4); (6) $R^6$ is phenyl, wherein said phenyl is optionally substituted by one, two or three substituents independently selected from halogen, preferably fluorine or chlorine, $CF_3$, $C_1$ to $C_4$ alkoxy, $OCF_3$, $NO_2$, or $NR^{10}R^{11}$ with $R^{10}$ and $R^{11}$ being as defined above.

For the compounds of formula II, $R^1$ and $R^7$ are preferably hydrogen.

For the compounds of formula II, preferably when R6 is mono-substituted phenyl said substitutent is in the 3- or 4-position and said substituent is selected from fluorine, chlorine, methoxy or trifluoromethoxy, and when $R^6$ is disubstituted phenyl said substitutents are in the 3,5-positions and said substituents are the same and are selected from fluorine, chlorine, methoxy or trifluoromethoxy.

Certain compounds of the invention may exist in different isomeric (e.g., enantiomers and diastereoisomers) forms. The invention contemplates all such isomers both in pure form and in admixture, including racemic mixtures. Enol forms are also included.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Certain basic compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate.

The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Numerous chemical substances are known to have histamine $H_1$ receptor antagonist activity. Many useful compounds can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine (also known as SCH-34117), diphenhydramine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

For example, the $H_3$ antagonists of this invention can be combined with an $H_1$ antagonist selected from astemizole, azatadine, azelastine, brompheniramine, cetirizine, chlorpheniramine, clemastine, carebastine, descarboethoxyloratadine (also known as SCH-34117), diphenhydramine, doxylamine, ebastine, fexofenadine, loratadine, levocabastine, mizolastine, norastemizole, or terfenadine.

Also, for example, the $H_3$ antagonists of this invention can be combined with an $H_1$ antagonist selected from, azatadine, brompheniramine, cetirizine, chlorpheniramine, carebastine, descarboethoxyloratadine (also known as SCH-34117), diphenhydramine, ebastine, fexofenadine, loratadine, or norastemizole.

Representative combinations include: the $H_3$ antagonists of this invention with loratadine, $H_3$ antagonists of this invention with descarboethoxyloratadine, $H_3$ antagonists of this invention with fexofenadine, and $H_3$ antagonists of this invention with cetirizine.

Those skilled in the art will know that the term "upper airway" means the upper respiratory system—i.e., the nose, throat, and associated structures.

The compounds of this invention may be prepared according to suitable processes known in the art for making similar compounds, e.g. processes described in the literature referred to above.

The following processes may be employed to produce compounds of Formula I. Unless stated otherwise, reactions are conducted at an appropriate temperature which allows the reaction to proceed at a reasonable rate to completion.

GENERAL PREPARATION SCHEMES

In general the compounds of this invention are prepared by first providing starting compounds of the general formula

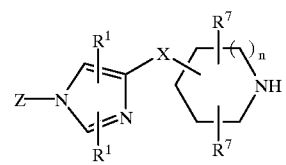

which then in a further step are reacted with a compound of the general formula

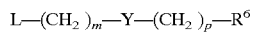

followed by elimination of the protecting group Z to yield a compound of formula I.

In the above formulae $R^1$, $R^6$, $R^7$, X, Y, m, n and p are as defined for formula I above. L represents a leaving group such as Cl, Br, I, and activated versions of OH such as $OSO_2CF_3$ generated independently or in situ.

The following reaction schemes illustrate the various steps of the processes used.

Preparation of Piperidines (n=1)

Reaction Scheme 1
Compounds wherein X is —(CH$_2$)$_{1-7}$

Step 1

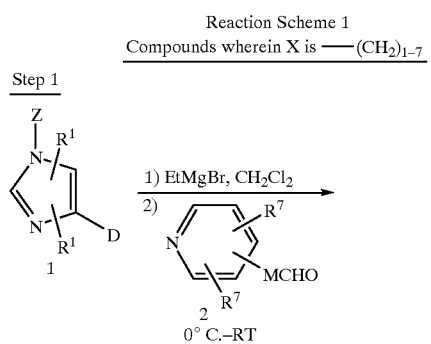

Compound 1, wherein (1) D is halogen, preferably iodide, (2) Z represents a protecting group such as triphenylmethyl, 2-(trimethylsilyl)-ethoxymethyl and the like, and (3) R$^1$ can be either hydrogen, alkyl or trihalomethyl, is dissolved in a suitable solvent, such as methylene chloride, and treated with a Grignard reagent, such as ethylmagnesium bromide. Subsequent addition of an appropriate aldehyde 2 (M=(CH$_2$)$_{0-6}$) produces compound 3.

Step 2

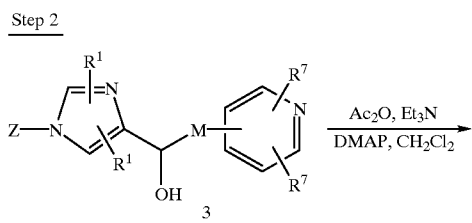

In step 2, compound 3 is dissolved in an organic solvent, such as methylene chloride, and treated with a tertiary amine base, such as triethylamine, and an acylation catalyst, such as dimethylaminopyridine. Subsequent treatment with acetic anhydride provides the compound of formula 4.

Step 3

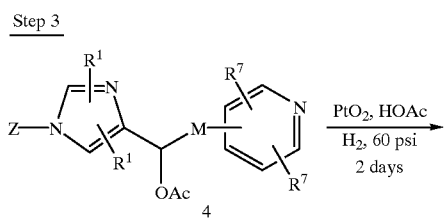

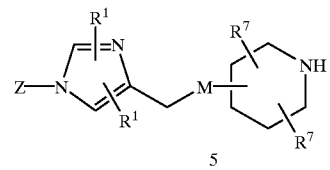

In step 3, compound 4 is dissolved in a suitable organic acid, such as acetic acid, and hydrogenated under pressure (16–60 psi) in the presence of an appropriate catalyst, such as platinum oxide, to provide compound 5.

Reaction Scheme 2
Compounds wherein X is —(CH$_2$)$_2$—

Step 1

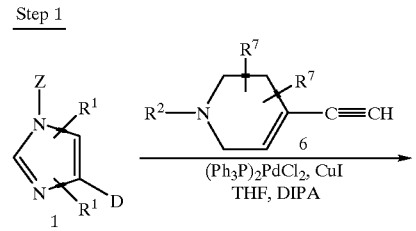

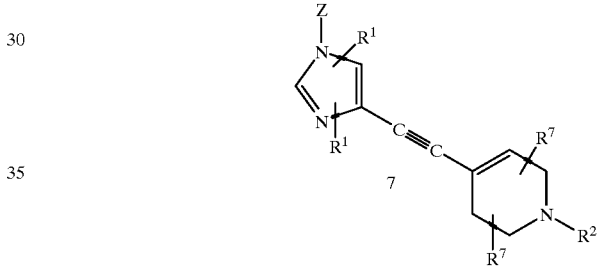

In Step 1, compound 1, wherein (1) D=halogen, preferably iodide, (2) Z represents a protecting group such as triphenylmethyl, 2-(trimethylsilyl)ethoxymethyl and the like, and (3) R$^2$ represents benzyl or substituted benzyl, is dissolved in a suitable solvent or a mixture of solvents selected from ethereal and dialkylamine solvents. A tetrahydrofuran/diisopropyl-amine mixture is preferred. Addition of a compound of structure 6 followed by addition of a suitable catalyst, such as bistriphenylphosphine-palladium dichloride and copper iodide, and stirring at temperatures from 21–60° C. provides compound 7.

Step 2

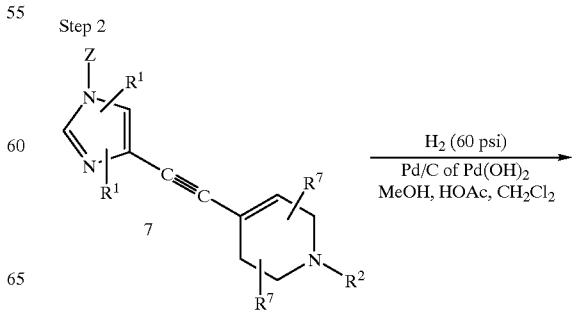

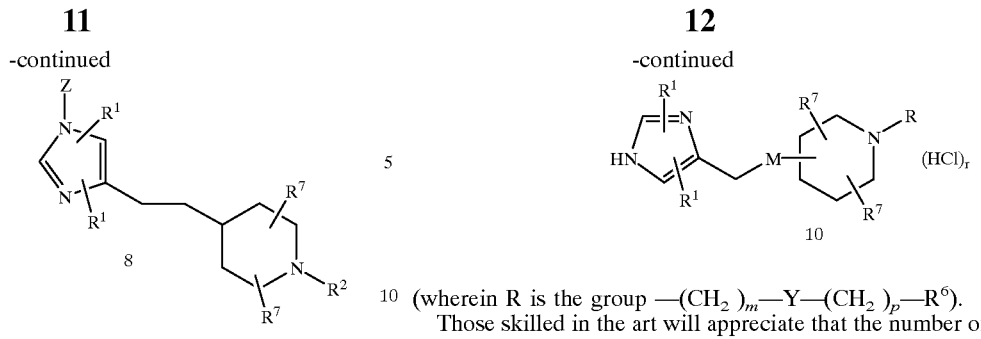

In Step 2, compound 7 is dissolved in a suitable organic solvent or mixtures thereof (examples of solvents include methylene chloride, methanol, and acetic acid) and hydrogenated with a catalyst, such as palladium or palladium hydroxide, at pressures ranging from 16–60 psi to provide compound 8.

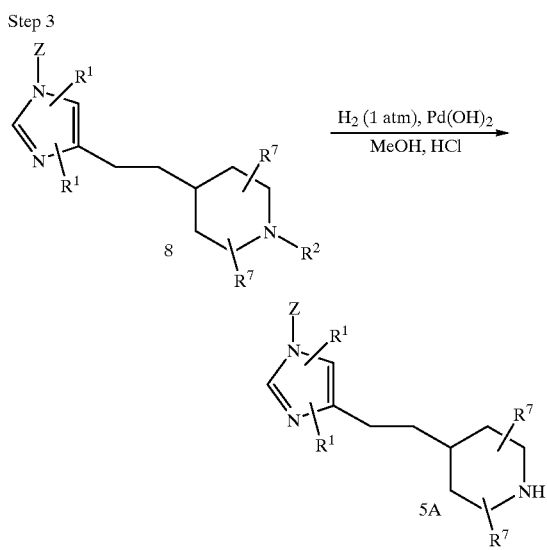

In Step 3, compound 8 is dissolved in a suitable alcohol, such as methanol, and treated with a few drops of hydrochloric acid (1M) and hydrogenated with a suitable catalyst, such palladium or palladium hydroxide, at pressures ranging from 16–60 psi to provide compound 5A.

Reaction Scheme 3 - Preparation of Compound 10

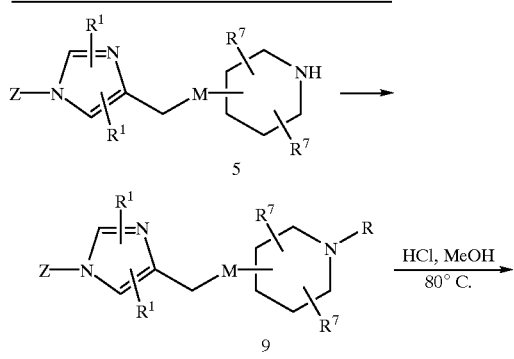

(wherein R is the group —$(CH_2)_m$—Y—$(CH_2)_p$—$R^6$).

Those skilled in the art will appreciate that the number of HCl molecules (r) is based on the number of basic groups present in compound 10.

Compound 5 is reacted with L—$(CH_2)_m$—Y—$(CH_2)_p$–$R^6$ to produce compound 9. L is a leaving group, such as Cl, Br, I and activated versions of OH, such as $OSO_2CF_3$ generated independently or in situ. When Y is —C(O)NH—, —OCO and —$SO_2$—, and m is 2, then compound 5 is reacted with reactants such as $(CH_2$=$CH)$ $C(O)O(CH_2)_pR^6$, $(CH_2$=$CH)C(O)NR^5(CH_2)_pR^6$, and $(CH_2$=$CH)SO_2(CH_2)_pR^6$.

The reactions are conducted in suitable solvents, such as ether, tetrahydrofuran, dioxane, dimethylsulfoxide, dimethylformamide, water, methylene chloride, and toluene, with or without the presence of a suitable bases, such as triethylamine, lithium diisopropylamide or sodium hydride, at temperatures ranging from −78° to 200° C.

When Z is triphenylmethyl, compound 9 is deprotected by treatment with dilute aqueous acid, such as HCl or HBr, at a temperature of about 25° to 100° C. to produce compound 10. Other protecting groups are removed by methods well known in the art.

Preparation of Compounds Having A 7-Membered Heterocyclic Ring

Reaction Scheme 4 - Compounds wherein X is —$CH_2$—

Step 1

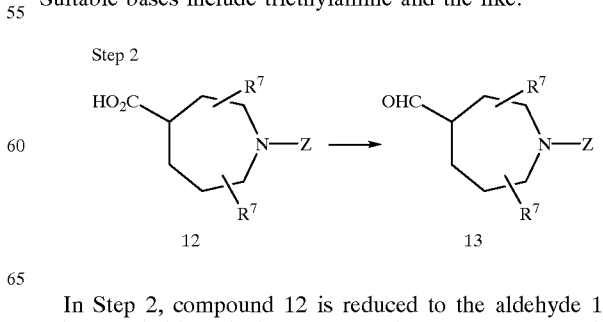

In Step 1, compound 11 (prepared in an analogous manner to the procedures outlined in *European J. Med Chem.* 1979,14, 157–164 and *Tetrahedron Letts.* 1990, 31, 933–936) is reacted with a compound ZCl in a suitable organic solvent at a temperature of from 0° to about 50° C. in the presence of an organic base to produce compound 12. Z represents a protecting group, preferably carbobenzyloxy. Suitable solvents include THF, ether, dioxane or the like. Suitable bases include triethylamine and the like.

Step 2

In Step 2, compound 12 is reduced to the aldehyde 13 using a suitable reducing agent, such as $BH_3 \cdot SMe_2$ or the like, in a suitable organic solvent, such as THF, ether, dioxane or the like, at a temperature of 0° to 100° C.

Step 3

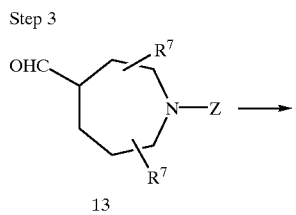

13

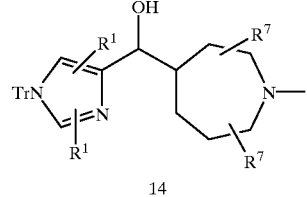

14

In Step 3, compound 13 is reacted with the Grignard reagent formed from iodoimidazole in the same manner as described for Step 1 of Reaction Scheme 1 to give the alcohol 14.

Step 4

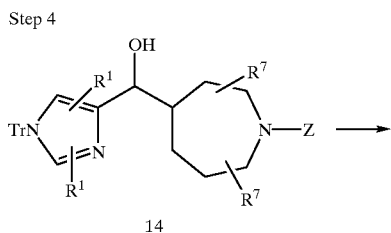

14

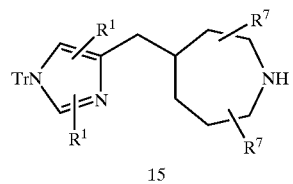

15

In Step 4, compound 14 is reduced to compound 15 in a suitable polar organic solvent using $H_2$ in the presence of a metal catalyst and a trace of acid at a temperature of from 25° to 75° C. Suitable solvents include MeOH, EtOH and i-PrOH, with EtOH being preferred, and catalysts can include Pd/C or $PtO_2$ or the like.

Step 5

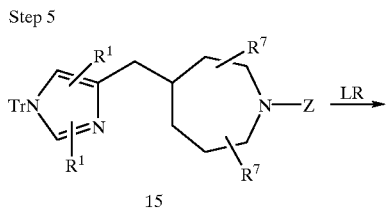

15

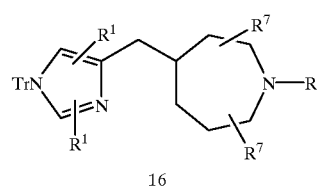

16

In Step 5, compound 15 is reacted with LR in a suitable solvent such as THF, ether, or the like in the presence of a suitable tertiary amine base such as triethylamine at a temperature from 0° to 100° C., preferably 25° C., to produce compound 16. R is —$(CH_2)_m$—Y—$(CH_2)_p$—$R^6$ and L is a leaving group as defined in Reaction Scheme 3 above.

Step 6

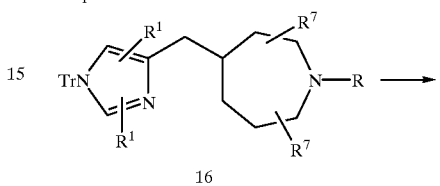

16

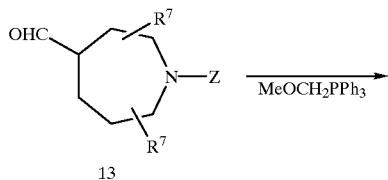

17

Step 6 is performed in a similar manner to the deprotection step in Reaction Scheme 3 above to give compound 17.

Reaction Scheme 5 - X is —$(CH_2)_2$—

Step 1

13

19

In Step 1, aldehyde 13 is reacted with the Wittig reagent in a suitable ethereal solvent in the presence of a strong base at a temperature from −25° to 80° C. to give compound 19. Suitable solvents include THF, ether, dioxane or the like. Strong bases can include lithium or potassium diisopropylamide, and lithium, sodium or potassium bis(trimethylsilyl)amide or the like. Other suitable bases can include NaH or KH in a suitable polar aprotic solvent, such as DMSO.

Step 2

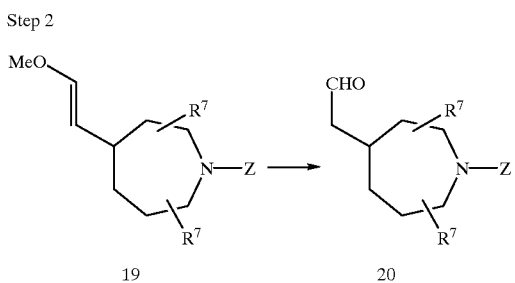

In Step 2, the enol ether 19 is hydrolyzed to the aldehyde 20 by treatment with a dilute mineral acid, such as HCl or HBr, at a temperature from 0° to about 80° C. Aldehyde 20 can then be converted to the desired targets in a manner similar to that described in Reaction Scheme 4, Steps 3 to 6.

Reaction Scheme 6 - X is ———$(CH_2)_3$——— to ———$(CH_2)_7$———

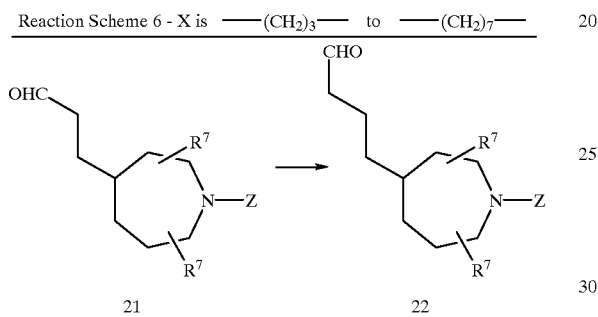

Aldehyde 20 can be converted to aldehyde 21 in a similar manner to that described in Reaction Scheme 5. Compound 21 can then be converted to the desired targets in a manner similar to that described in Reaction Scheme 4, Steps 3 to 6. A similar sequence can be applied to compound 22 and to higher homologs.

Preparation of Pyrrolidines (n=0)

Reaction Scheme 7

Step 1

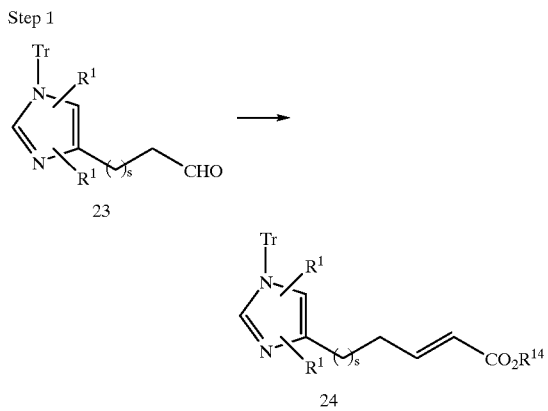

wherein s is 0 to 5, and $R^{14}$ represents lower alkyl (e.g., methyl or ethyl).

In Step 1, a suitable Horner-Emmons reagent such as trimethyl- or triethyl phosphonoacetate is treated with a strong base, such as NaH, KH, lithium diisopropylamide or the like, in a suitable ethereal solvent such as THF, ether, dioxane or the like. The phosphonate carbanion is then reacted with the aldehyde 23 for 30 min. to 24 h at a temperature suitable to complete the reaction and give ester 24.

Step 2

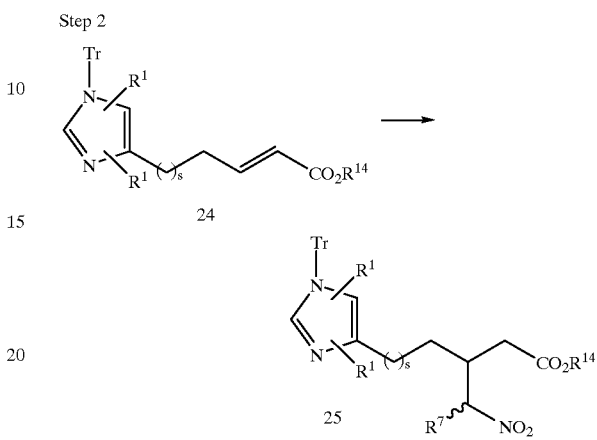

In Step 2, ester 24 is reacted with a substituted or unsubstituted nitroalkane, such as nitromethane or nitroethane, in a polar aprotic solvent, such as acetonitrile, THF or the like, preferably acetonitrile, in the presence of an amine base, such as DBU, DBN, triethylamine or the like, preferably DBU, at a temperature from 0° to 80° C., preferably 25° C., for 24 h to yield nitro ester 25.

Step 3

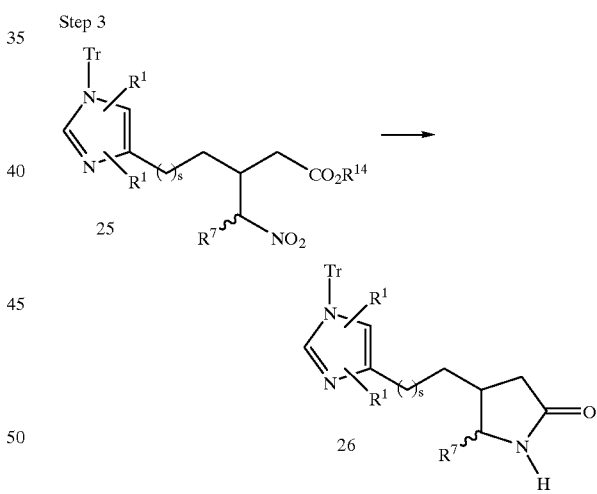

In Step 3, the nitro group of nitro ester 25 is reduced to the amine using hydrogen and a suitable metal catalyst, such as Pd/C, Ra—Ni or the like, in a suitable protic solvent, such as methanol, ethanol or the like, at a temperature of from 25° to 80° C. The resulting amino ester is cyclized to the lactam by heating in a suitable protic solvent, such as methanol or ethanol, at a temperature of up to 80° C. in the presence of a small amount of a base such as potassium carbonate or the like to give compound 26.

Step 4

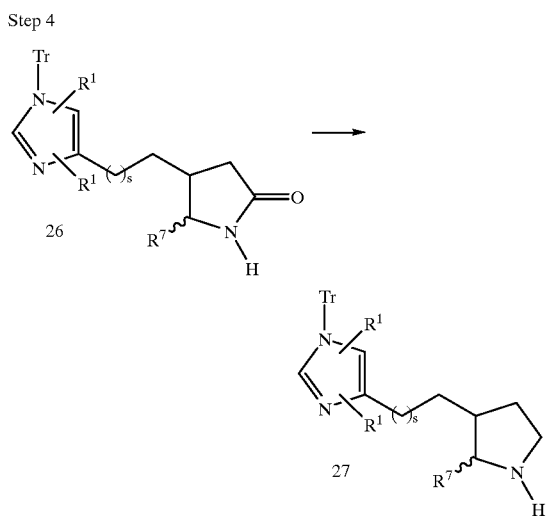

In Step 4, compound 26 is reacted with a suitable reducing agent, such as LAH, BH$_3$, or the like, preferably LAH, in a suitable solvent, such as THF, ether, dioxane or the like, at a temperature ranging from 0° to 80° C., preferably 60° C., for a time ranging from 30 min. to 24 h, preferably 3 h to give compound 27.

Compound 27 is then reacted with a compound of the formula L—(CH$_2$)$_m$—Y—(CH$_2$)$_p$—R$^6$ followed by deprotection in a manner similar to the procedure outlined for Reaction 3 above.

The starting compounds of formula 23 are either known compounds or may be obtained according to procedures well known in the art, for example by following the preparations in the steps outlined for compounds 13, 20, and 22 above.

A person skilled in the art will easily see that several variations of the above processes are possible. For example, the substituents R$^1$ and R$^7$ may be present in the starting materials or may be introduced at any convenient stage of the process.

The following examples are intended to illustrate, but not to limit, the present invention.

Example 1

Step A

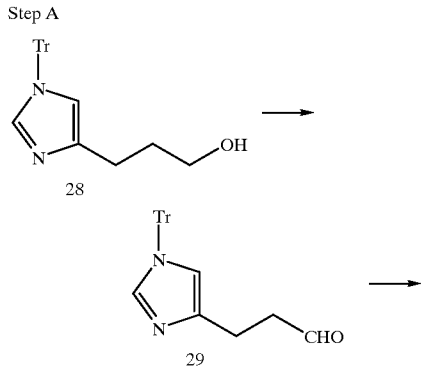

-continued

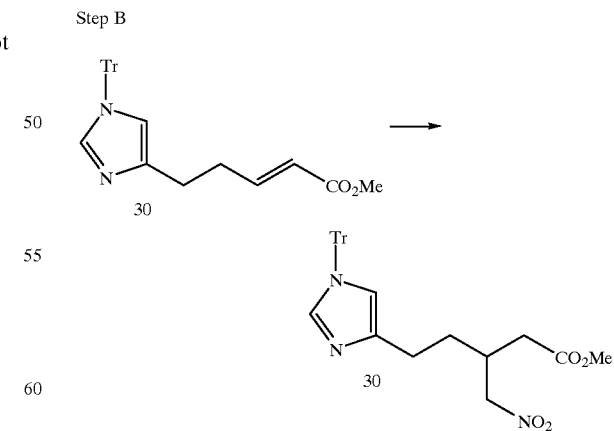

To a flask containing oxalyl chloride (13.8 g, 9.5 ml, 109 mmols) in methylene chloride (300 ml) at −78° C. was added DMSO (19.9 g, 255 mmols) dropwise. When gas evolution stopped, the mixture was stirred for 8 min., and a solution of the alcohol 28 (10.0 g, 27.2 mmols) in methylene chloride (50 ml) was added. The reaction was maintained at −78° C. for 50 min., triethylamine (45 ml, 255 mmol) was added, and the reaction allowed to warm to room temperature over 45 min. The contents were diluted with NH$_4$Cl solution and extracted with methylene chloride. The combined organics were washed with brine, dried over MgSO$_4$, filtered and concentrated. The crude product was chromatographed over silica gel (10 to 30% acetone in methylene chloride) to give the product 29 as a faint yellow oil (7.7 g, 77%): LRMS (Cl, M+H)=367.

To a flask containing NaH (95%, 2.0 g, 79 mmol), was added dry THF (600 ml) under a nitrogen atmosphere. To this mixture was added trimethylphosphonoacetate (14.0 g, 77.5 mmols) dropwise via syringe. Gas evolution was observed and a viscous white mixture resulted. The mixture was warmed to 35° C. for 30 min. and then allowed to cool back to room temperature. The aldehyde 29 (14.5 g, 39.6 mmols) in dry THF (200 ml) was added via syringe to the reaction mixture. TLC (40% EtOAc-Hex) indicated the reaction to be complete after stirring for 45 min. at r.t. The contents were diluted with water, and the aqueous portion was extracted with EtOAc. The combined organics were washed with brine, dried over MgSO$_4$, filtered and concentrated to give a solid which was recrystallized from Et$_2$O-hexane (1:2 v/v) to give 5.9 g of pure material. The mother liquors were chromatographed on silica gel (40% EtOAc-hexane→60% EtOAc) to afford another 7.7 g of material, 810% combined yield. LRMS (Cl, M+H)=423. Analytical CHN for (C$_{28}$H$_{26}$N$_2$O$_2$): C, 79.25; H, 6.22; N, 6.60: Found C, 79.11; H, 6.39; N, 6.66. mp=129–130.5° C.

Step B

To a CH$_3$CN solution (300 ml) of 30 (11.0 g, 26.1 mmols) was added CH$_3$NO$_2$ (29.3 g, 26 ml, 480 mmols) followed by DBU (5.1 g, 5.0 ml, 33.4 mmols). The reaction mixture was stirred under a nitrogen atmosphere for 18 h, at which time no starting material was observed by TLC (40% EtOAc-Hex). The solvents were evaporated under reduced pressure, and the residue was chromatographed directly on silica gel (50% EtOAc-Hex→70% EtOAc) affording 13.1 g (>100% crude yield) of the product as a colorless oil. LRMS (Cl, M+H)=484. Analytical CHN for ($C_{29}H_{29}N_3O_4$): C, 72.03; H, 6.04; N, 8.69: Found C, 72.06; H, 6.34; N, 8.66. mp=97.5–99.5° C.

Step C

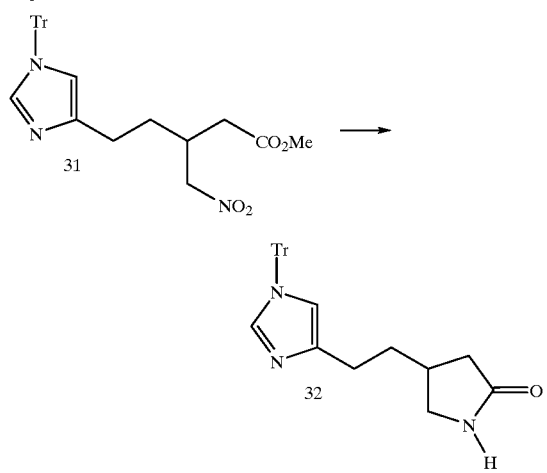

Compound 31 (2 x 5 g, 20.7 mmols) was dissolved in a solution of absolute EtOH-THF (60-20, v/v). Ra—Ni (~2×5 g) was added, and the Parr vessel was pressurized to 50 psi with hydrogen. After shaking for 4–6 h, TLC indicated the reduction to the amino-ester was complete (10% MeOH-EtOAc). The catalyst was removed by filtering through celite. Evaporation under reduced pressure afforded the amino-ester intermediate which was subsequently cyclized to the lactam by refluxing in MeOH with a small amount of $K_2CO_3$ for 3 h. Removal of the $K_2CO_3$ by filtration and evaporation of the solvent afforded an oil which was chromatographed on silica gel (10% MeOH—$CH_2Cl_2$→10% MeOH+2% $NH_4OH$) to give the product as an off white amorphous solid, 8.1 g (92%). LRMS (Cl, M+H)=422. Analytical CHN for ($C_{28}H_{27}N_3O×1.5$ mol $H_2O$): C, 74.91; H, 6.57; N, 9.36: Found C, 74.76; H, 6.17; N, 9.14. MP=171–173.5° C.

Step D

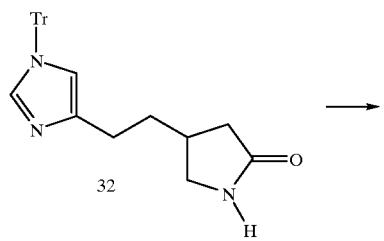

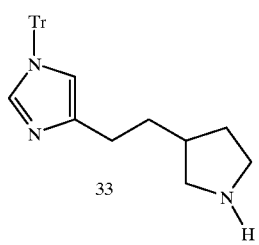

To a flask containing a THF (12 ml) solution of LAH (180 mg, 4.80 mmols, 10 equiv.) was added a THF solution of 32 at room temperature. The mixture was heated to 60° C. for 3 h, then allowed to cool to r.t. The reaction was quenched by the addition of solid $Na_2SO_4×10H_2O$. After 20 min. 5% NaOH (~1 ml) was added causing the viscous gray mixture to become colorless and homogeneous. After another 20 min. the mixture was filtered through celite and the filter cake was washed well with THF and MeOH. The effluent was concentrated under reduced pressure and then chromatographed on silica gel (10% MeOH—$CH_2Cl_2$→10% MeOH+2% $NH_4OH$) to afford 168 mg (73%) of the product 33 as hygroscopic foam. LRMS (Cl, M+H)=408.

Step E

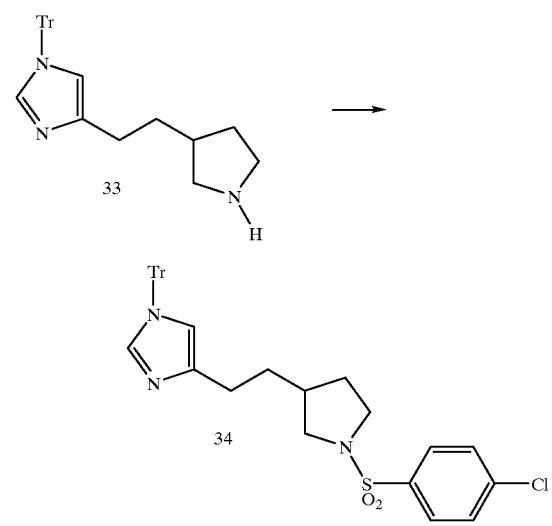

To a $CH_2Cl_2$ solution (6 ml) of (+/−)33 (315 mg, 0.774 mmols) was added $Et_3N$ (2 ml, 14.4 mmols) followed by p-chlorosulfonyl chloride (215 mg, 1.09 mmols) at r.t. The mixture was stirred under a nitrogen atmosphere for 21 h, then evaporated to 1/2 volume and chromatographed on silica gel (1% MeOH—$CH_2Cl_2$→3% MeOH) which afforded an amorphous white solid. Trituration with hexane-acetone followed by evaporation yielded a fluffy white foam. LRMS (Cl, M+H)=582.

Step F

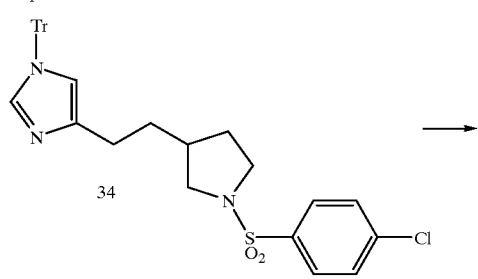

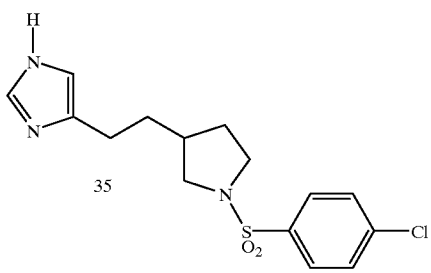

Standard HCl deprotection of 34 provides the hydrochloride salt of 35 as a light tan solid. LRMS (Cl, M+H)=340.

Example 1A

Chiral Synthesis

Step A

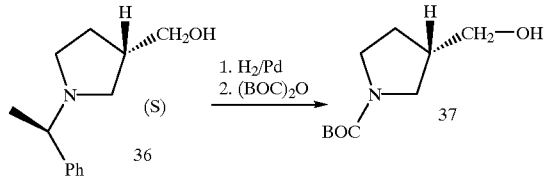

A solution of 36 (2.0 g) in ethanol (20 ml) and 10% palladium-on-carbon (0.3 g) is hydrogenated in a Parr shaker at 60 psi for 24 hr. The catalyst is then filtered and the filtrate is evaporated under reduced pressure. The residual oil is dissolved in dichloromethane (20 ml). Di-tert butyl-dicarbonate (2 g) is added to the solution followed by 4-dimethyl-aminopyridine (0.05 g). The reaction mixture is stirred at 70° C. for 1 hour and is then evaporated under reduced pressure. The product is then flash chromatographed on silica gel (50 ml). Elution with 8% methanol-dichloromethane afforded after evaporation under reduced pressure the title compound 37 as a colorless oil (1.1 g), MS (Cl) m/e=146 (M-56).

Step B

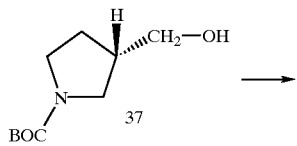

-continued

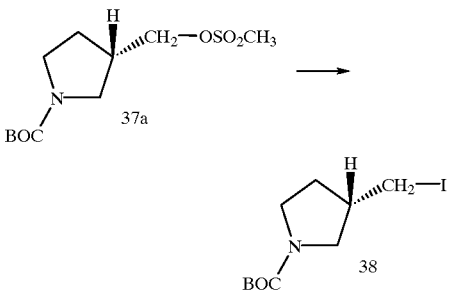

A solution of 37 (1.1 g) and triethylamine (0.84 ml) in dichloromethane is cooled in an ice-bath and stirred while adding dropwise a solution of mesyl chloride (0.47 ml) in dichloromethane (5 ml). The reaction mixture is stirred for 1 hour and is then washed with water, dried over sodium sulfate and filtered through a silica-gel plug. The filtrate is evaporated to afford the mesylate 37a which is then dissolved in acetone (30 ml) containing sodium iodide (1.6 g). The reaction mixture is heated with stirring in an oil-bath (70° C.) for 24 hours and then cooled. The insoluble salts are removed by filtration and the filtrate is evaporated under reduced pressure. The residual product is dissolved in dichloromethane and washed with water, dried over sodium sulfate and filtered through a silica-gel plug. The filtrate is evaporated under reduced pressure to afford the title compound 38 as an oil (1.53 g), MS (FAB) m/e 280 (MH)$^+$.

Step C

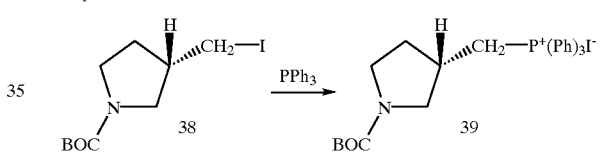

A solution of 38 (1.53 g) and triphenylphosphine (1.9 g) in dimethylformamide (10 ml) is heated in an oil-bath (90° C.) for 24 hr. The reaction mixture is then evaporated under reduced pressure and the residual product is flash chromatographed on silica-gel (50 ml). Elution with 10% methanol-dichloromethane afforded after evaporation under reduced pressure the title compound 39 as a white powder (1.56 g), MS (FAB) m/e=446 (M)$^+$.

Step D

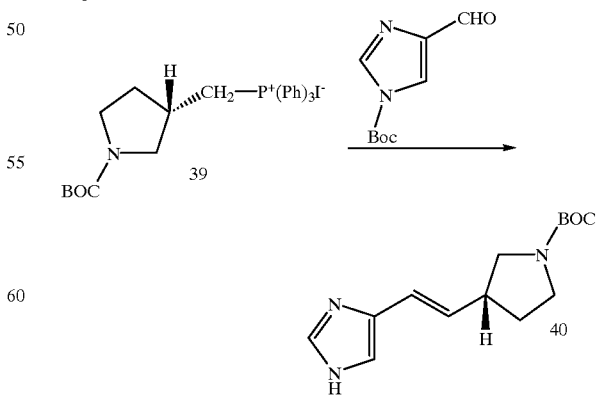

2.5M butyllithium solution in hexanes (0.9 ml) is added to a solution of 39 (1.0 g) in tetrahydrofuran (10 ml) at −78°.

The solution is then stirred at room temperature for 30 minutes and the resulting solution is re-cooled to −78° followed by the addition of a solution of the aldehyde (0.38 g) in tetrahydrofuran (5 ml). The reaction mixture is the filtered and the filtrate is evaporated under reduced pressure. The resulting crude product is flash chromatographed on silica-gel (50 ml). Elution with 5% methanol-dichloromethane afforded after evaporation under reduced pressure the title compound 40 as a white powder (0.34 g), MS (FAB) m/e=264 (MH)+.

Step E

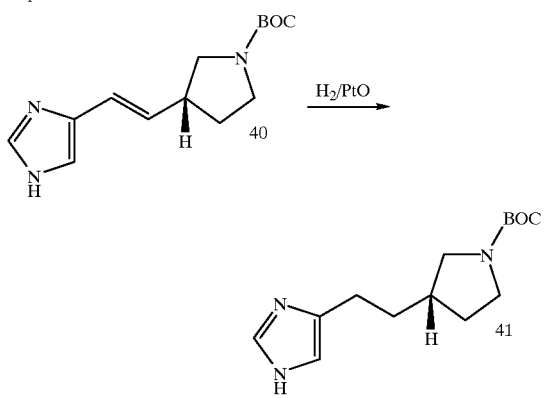

A solution of 40 (0.32 g) in ethanol (5 ml) containing PtO (0.085 g) is hydrogenated at atmospheric pressure for 24 hours. The catalyst is then filtered and the filtrate is evaporated under reduced pressure. The resulting crude product is flash chromatographed on silica-gel (30 ml). Elution with 10% methanol-dichloromethane afforded after evaporation under reduced pressure the title compound 41 as a resinous gum (0.23 g), MS (FAB) m/e=266 (MH)+.

Step F

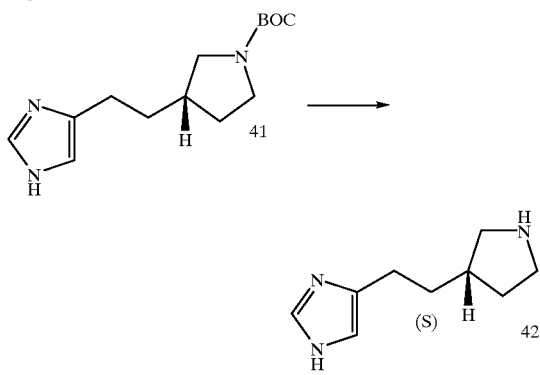

Compound 41 (0.1 g) is stirred with 4M HCl in dioxane (2 ml) for 30 minutes and the reaction mixture is then evaporated under reduced pressure. The residual product is dissolved in methanol (2 ml) and the solution is stirred while adding Biorad AG 1-X8 (OH⁻ form) ion-exchange resin until the pH of the solution is above 8. The resin is removed by filtration and the filtrate is then evaporated to afford the title compound 42 as a resinous gum (0.061 g), MS (CI) m/e=165 (MH)+.

The R-enantiomer can be obtained in a similar manner.

Example 2

Step A

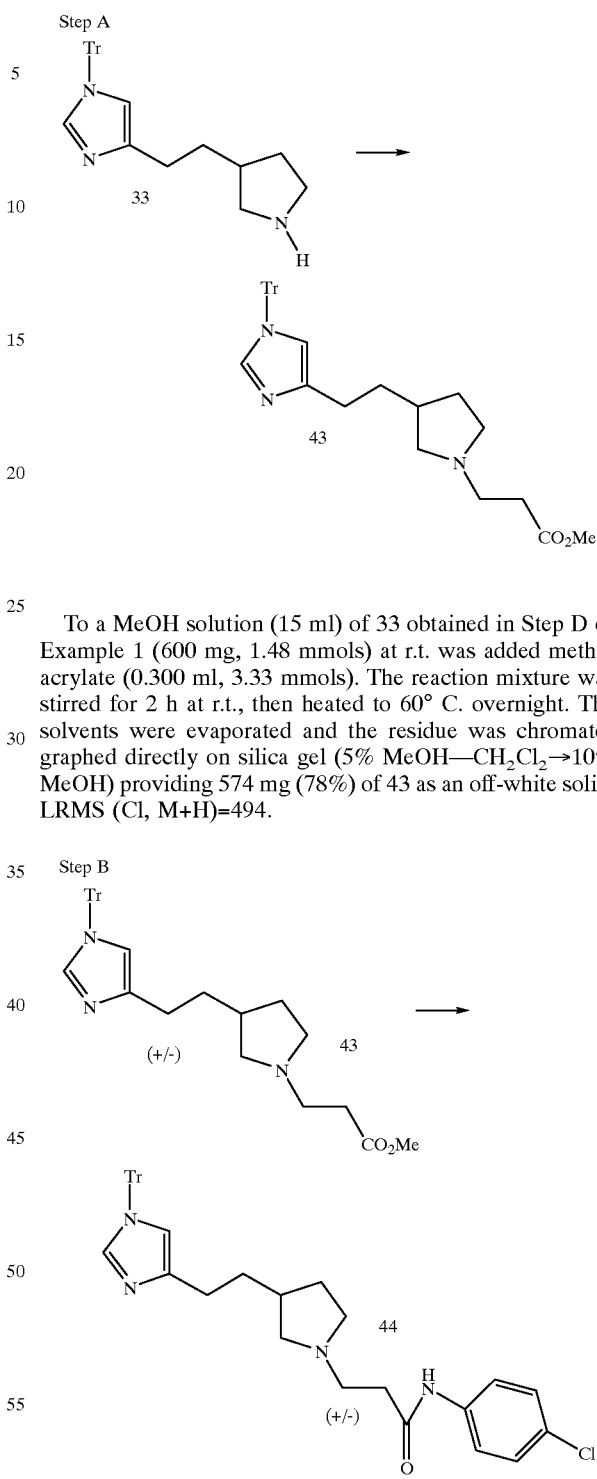

To a MeOH solution (15 ml) of 33 obtained in Step D of Example 1 (600 mg, 1.48 mmols) at r.t. was added methyl acrylate (0.300 ml, 3.33 mmols). The reaction mixture was stirred for 2 h at r.t., then heated to 60° C. overnight. The solvents were evaporated and the residue was chromatographed directly on silica gel (5% MeOH—CH₂Cl₂→10% MeOH) providing 574 mg (78%) of 43 as an off-white solid. LRMS (CI, M+H)=494.

Step B

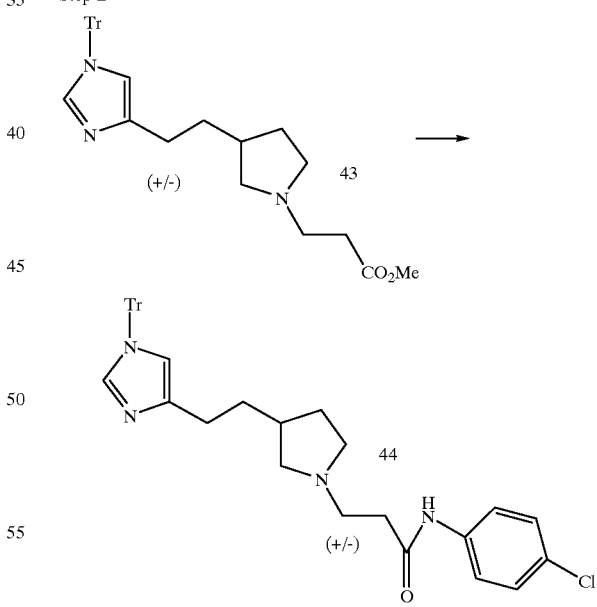

To a toluene (5 ml) solution of p-chloroaniline (0.160 g, 1.25 mols) was added trimethylaluminum (0.700 ml, 2M in toluene) at 0° C. The mixture was stirred at 0° C. for 15 min., and at r.t. for 40 min. Then a toluene—CH₂Cl₂ solution of the compound 43 (10 ml, 1:1, v/v) was added at 0° C. to the aniline complex. After 30 min., the mixture was heated to 80° C. for 3 h, and left at r.t. overnight. The reaction was quenched by the addition of solid Na₂SO₄×10 H₂O, followed by the addition of MeOH. After stirring for 20 min., the mixture was filtered through celite, and concentrated under reduced pressure. Chromatography on silica gel (10% MeOH-EtOAc→15% MeOH with 1% NH$_4$OH) gives 624 mg (97%) of 44 as a white foam. Irms (Cl, M+H)=589.

Step C

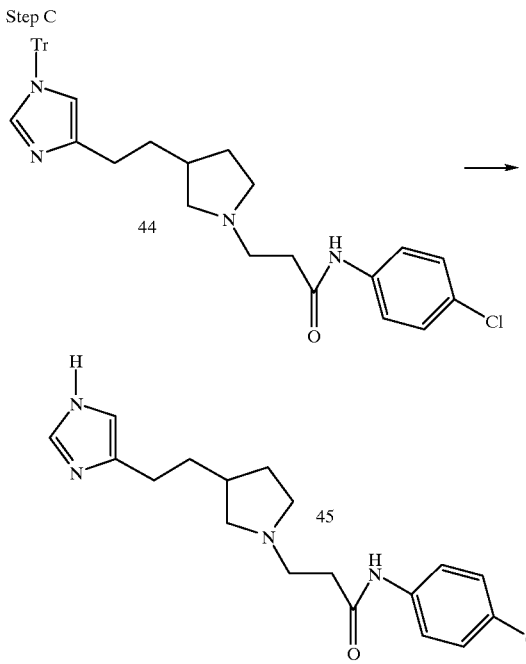

To a dioxane solution (10 ml) of the compound 44 from the previous step was added a solution of 4M HCl-dioxane (2×2 ml) and the mixture was heated to 80° C. for 6 h. The mixture was cooled to r.t., and evaporated under reduced pressure affording a gummy foam. The residue was rinsed with Et2O (3×10 ml) and the supernatant was decanted. The product was stored under high vacuum affording 45 as a tan solid (400 mg of dihydrochloride salt). MS(Cl) 347 (M+1).

Example 3

Step A

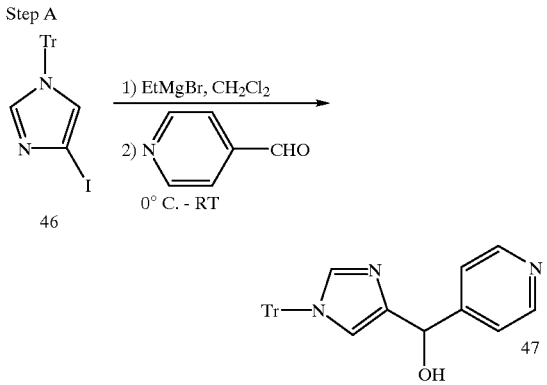

Ethylmagnesium bromide (23 mL, 69.1 mmol, 3M in ether) was dropwise added to a 0° C. solution of 4-iodo-triphenylmethylimidazole (25.1 g, 57.6 mmol) in methylene chloride (280 mL). The mixture was stirred at 0° C. for 30 min., the cooling bath was removed and the resulting yellow solution was stirred at room temperature for 60 min. 4-pyridine-carboxaldehyde (6.1 ml, 63.4 mmol) was added dropwise. The reaction becomes very thick. A small aliquot of the reaction mixture is partitioned between ethyl acetate and saturated ammonium chloride. TLC (5% methanol/methylene chloride) indicated consumption of starting material. The reaction was quenched with saturated ammonium chloride. The resulting mixture was dissolved in methylene chloride (required ~1.5 L), transferred to a separatory funnel, and extracted with methylene chloride. The extracts were combined, washed with brine, dried over anhydrous sodium sulfate, filtered and concentrated onto enough silica gel such that a free flowing powder was obtained. The powder was loaded onto a chromatography column pre-packed with 10% methanol/methylene chloride. Elution with the same solvent provided 22.5 g (93%) of 47 as a white solid. NMR $^1$H (400 MHz, CDCl$_3$): 8.56(2H, d, J=6.0 Hz), 7.47(1H, d, J=1.4 Hz), 7.36(11H, m), 7.13(6H, s), 6.63(1H, s), 5.79(1H, s), 4.43(1H, s). MS (Cl): 418 (M+1, 26), 243(100), 167(45).

Step B

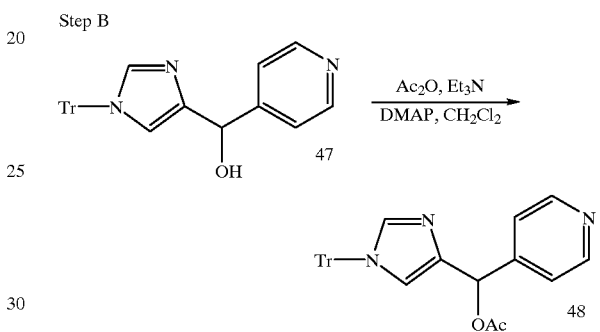

Acetic anhydride (9.7 mL, 51.4 mmol) was added to a room temperature suspension of 47 (21.4 g, 51.1 mmol), triethylamine (35.6 ML, 255.7 mmol) and dimethylaminopyridine (0.13 g, 1.0 mmol) in ethylene chloride (800 mL). The suspension was allowed to stir overnight. All of the solid eventually dissolves. TLC (10% methanol/methylene chloride) indicated consumption of starting material. The mixture was transferred to a separatory funnel, diluted with methylene chloride, washed with saturated ammonium chloride and brine, dried over anhydrous sodium sulfate and filtered. The filtrate was concentrated and the resulting residue was azeotroped (3X) with toluene (to remove residual acetic acid and acetic anhydride) to give 22.8 g (97%) of 48 as a white solid. NMR $^1$H (400 MHz, CDCl$_3$): 8.61(2H, d, J=6.1 Hz), 7.46(1H, d, J=1.4 Hz), 7.38(11H, m), 7.15(6H, s), 6.83(1H, s), 6.80(1H, s), 2.20 (3H, s).

Step C

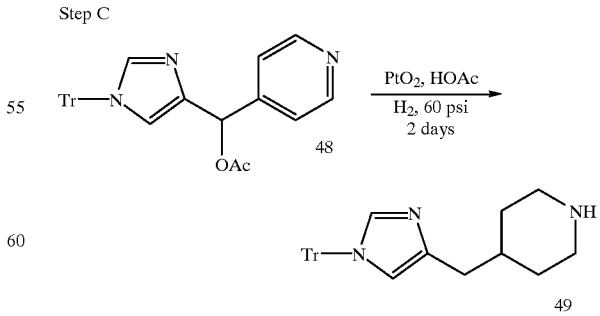

48 was dissolved in acetic acid (100 mL) with warming, transferred to a Parr hydrogenation flask and purged with nitrogen. Platinum oxide (1.13 g, 4.96 mmol) was added.

The resulting mixture was hydrogenated on a Parr apparatus at 60 psi overnight. A small aliquot was quenched into 1 N NaOH and ethyl acetate. TLC (10% MeOH/methylene chloride) indicated consumption of starting material and the formation of lower R$_f$ products. The mixture was resubmitted to hydrogenation for an additional day. TLC indicated consumption of starting material. The mixture was filtered through celite and concentrated. The residue was partitioned between 1N sodium hydroxide and methylene chloride. Solid sodium chloride was added to increase separation and the mixture was extracted with methylene chloride. The extracts were combined, washed with brine, dried over anhydrous sodium sulfate and concentrated onto enough silica gel such that a free flowing powder results. This powder was loaded onto a chromatography column prepacked with silica and 10% methanol/methylene chloride. Elution with 5% NH$_4$OH$_{(conc.)}$/10% methanol/85% dichloromethane to give 15.9 g (79%) of 49 as a white glass. NMR $^1$H (400 MHz, CDCl$_3$): 7.33(10H, m), 7.14(6H, m), 6.51 (1H, s), 3.04(2H, m), 2.57(2H, dd, J=2.4,12.1 Hz), 2.44(2H, d, J=7.0 Hz), 1.76(1H, ), 1.66(2H, d, J=12.5 Hz), 1.10(2H, dd, J=3.7,12.4 Hz). MS (LC/MS): 08 (M+)

Step D

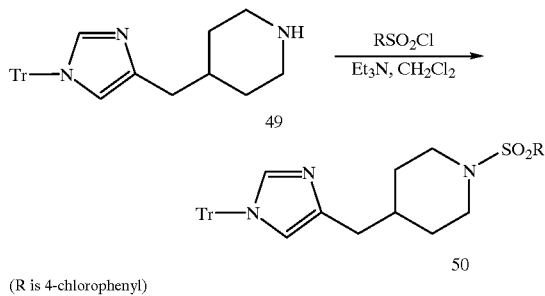

(R is 4-chlorophenyl)

4-Chlorobenzenesulfonyl chloride (0.12 g, 0.56 mmol) was added to a room temperature solution of 49 (0.21 g, 0.51 mmol) and triethylamine (0.11 ml, 0.76 mmol) in methylene chloride (3 ml). The resulting mixture was stirred overnight. TLC (10% methanol/methylene chloride) indicated consumption of starting material. The solution was transferred to a separatory funnel, diluted with methylene chloride, washed with water and brine, dried over anhydrous sodium sulfate, filtered and concentrated onto enough silica gel such that a free flowing powder was obtained. The resulting powder was loaded onto a chromatography column prepacked with silica and methylene chloride. Elution with methylene chloride followed by 10% methanol/methylene chloride gave 0.26 g of 50 as a white solid. NMR $^1$H (400 MHz, CDCl$_3$): 7.68(2H, d, J=8.6 Hz), 7.49(2H, d, J=8.5 Hz), 7.32(10H, m), 7.12(6H, m), 6.49(1H, s), 3.74(2H, d, J=11.5 Hz), 2.41(2H, d, J=7.0 Hz), 2.24(2H, dd, J=2.36, 11.8 Hz), 1.69(2H, d, J=13.0 Hz), 1.61 (1H, m), 1.28(2H, dd, J=4.2, 12.8 Hz). MS (LC/MS): 582 (M+).

Step E

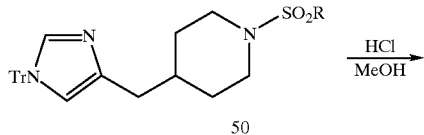

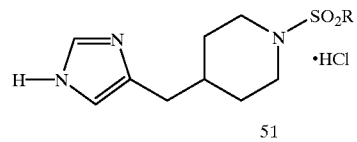

A mixture of 50 (0.299 g, 0.56 mmol) in methanol (6 ml) and 1N HCl (3 ml) was warmed to 80° C. After 3 h a small aliquot was quenched into 1N sodium hydroxide and ethyl acetate. TLC (10% methanol/methylene chloride) indicated consumption of starting material. The mixture was cooled to room temperature and concentrated. The residue was dissolved in water and ether and transferred to a separatory funnel. The water layer as washed with ether. The aqueous layer was concentrated to give 0.154 g (75%) of 51 as a glass. NMR $^1$H (400 CD$_3$OD): 8.80(1H, d, J=1.4 Hz), 7.75(2H, d, J=8.8 Hz), 7.62(2H, d, J=8.8 Hz), 7.32(1H, s), 3.77(d, J=11.8 Hz), 2.66(2H, d, J=7.2 Hz), 2.29(2H, DT, J=2.5,12.1 Hz), 1.73(2H, d, J=11.7 Hz), 1.60(1H, m), 1.32 (2H, m). MS (Cl): 340 (M+1)

Example 4

Step A

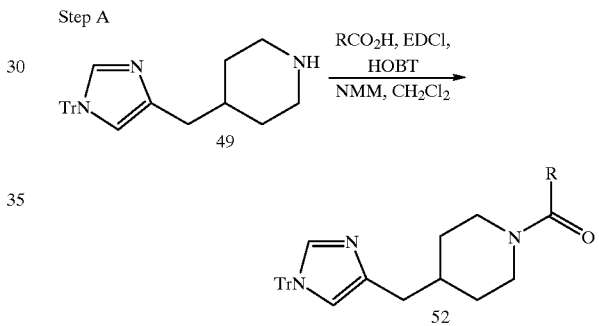

R is 4-chlorophenyl. 1-3-(Dimethylaminopropyl)-3-ethylcarbodiimide hydrochloride (0.20 g, 0.68 mmol) was added to a room temperature solution of 49 (0.21 g, 0.52 mmol), 4-chlorobenzoic acid (0.07 g, 0.57 mmol), N-methylmorpholine (0.17 ml, 1.56 mmol) and hydroxybenzotriazole (0.08 g, 0.62 mmol) in dimethylformamide (2 ml) and methylene chloride (2 ml). The resulting mixture was stirred overnight. TLC (10% methanol/methylene chloride) indicated consumption of starting material. The mixture transferred to a separatory funnel, diluted with methylene chloride, washed with water and brine, dried over anhydrous sodium sulfate, filtered and concentrated onto enough silica gel such that a free flowing powder was obtained. The resulting powder was loaded onto a chromatography column prepacked with silica and 10% methanol/methylene chloride. Elution with the same solvent gave 0.26 g of a clear oil. NMR shows the product was contaminated with dimethylformamide. The product was dissolved in ethyl acetate, washed with water, dried over anhydrous sodium sulfate, filtered and concentrated to give 0.237 g (83%) of 52. NMR $^1$H (400 MHz, CDCl$_3$): 7.34(14H, m), 7.13(6H), 6.52(1H, s), 4.65(1H, m), 3.68(1H, m), 2.98(1H, m), 2.74(1H, m), 2.47(2H, d, J=7 Hz), 1.96 (1H, m), 1.70(2H, m), 1.16(2H, m). MS (LC/MS): 546 (M+).

Example 5

Step A

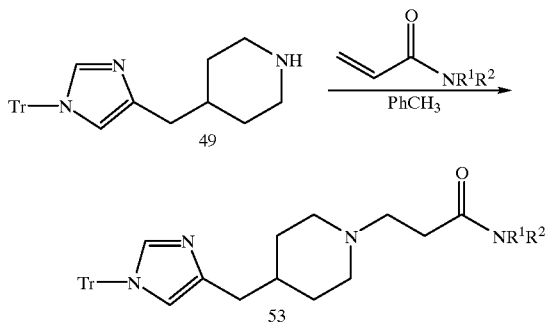

$R^1$ is H and $R^2$ is 4-chlorophenyl. A mixture of 49 (2.0 g, 4.9 mmol) and N-(4-chlorophenyl)acrylamide (0.98 g, 5.4 mmol) in toluene (50 ml) was heated to reflux overnight. TLC (10% methanol/methylene chloride) indicated consumption of starting material. The mixture was cooled to room temperature and concentrated onto enough silica gel such that a free flowing powder was obtained. The resulting powder was loaded onto a chromatography column prepacked with silica and 10% methanol/methylene chloride. Elution with 10% methanol/methylene chloride followed by 5% ammonia (conc)/10% methanol/85% methylene chloride gave 1.17 g of the title compound with a trace of impurity and 1.50 g of pure 53 as oils. Combined yield 2.67 g (92%). NMR $^1$H (400 MHz, CDCl$_3$): 7.46(2H, d, J=11.8 Hz), 7.34(1H, s), 7.32(10H, m), 7.23(2H, d, J=11.8 Hz), 7.14(6H, m), 6.55(1H, s) 3.04(2H, d, J=15.3) 2.68(2H, m), 2.51(4H, d, J=8.3 Hz), 2.07(2H, t, J=14.7 Hz), 1.80(3H, m), 1.28 (2H, m). MS (LC/MS): 589 (M+).

Example 6

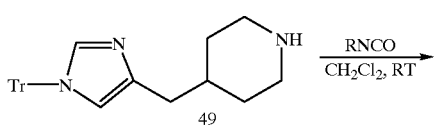

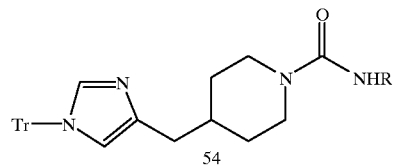

R is 3,5-dichlorophenyl. 3,5-dichlorophenylisocyanate (0.21 g, 1.1 mmol) was added to a room temperature solution of 49 (0.3 g, 0.74 mmol) in methylene chloride (5 ml). The resulting mixture was stirred overnight. TLC (5% ammonia (conc)/10% methanol/85% methylene chloride) indicated consumption of starting material. The mixture was concentrated onto enough silica gel such that a free flowing powder was obtained. The resulting powder was loaded onto a chromatography column prepacked with silica and 20% acetone/methylene chloride. Elution with 20% acetone/methylene chloride followed by 5% methanol/methylene chloride gave 0.37 g (83%) of 54 as a white solid. NMR $^1$H (400 MHz, CDCl$_3$): 7.53(1H, m), 7.36(10H, m), 7.12(6H, m), 6.97(1H, m), 6.71(1H, m), 6.56(1H, s), 4.04(2H, d, J=17.3 Hz), 2.86(2H, m), 2.52(2H, d, J=9.1 Hz), 1.95(1H, m), 1.72(2H, d, J=17.1 Hz), 1.16(2H, m). MS (LC/MS): 596 (M+).

Example 7

Step A

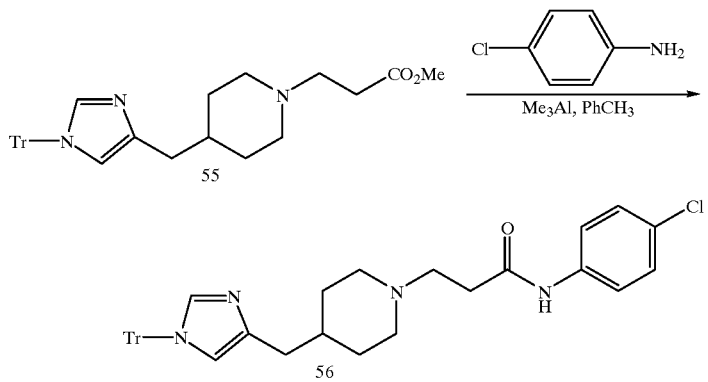

Trimethylaluminum (1.2 ml, 2.4 mmol, 2M in toluene) was added to a 0° C. solution of 3-chloroaniline (0.10 g, 0.8 mmol) in toluene (7.5 ml). After 5 minutes the cooling bath was removed and the mixture was stirred at room temperature for 30 minutes. 55 (0.48 g, 0.1 mmol) in toluene (10 ml) was added via cannula. The mixture was refluxed overnight. TLC (10% methanol/85% methylene chloride) indicated consumption of starting material. The mixture was cooled to room temperature, diluted with ethyl acetate and quenched with a saturated solution of sodium sulfate. The resulting mixture was stirred overnight. The mixture was made basic with 1N NaOH (3 ml). The resulting mixture was transferred to a separatory funnel and extracted with ethyl acetate. The extracts were combined, washed with water and brine, dried over anhydrous sodium sulfate and concentrated onto enough silica gel such that a free flowing powder was obtained. The resulting powder was loaded onto a chromatography column prepacked with silica and 3% methanol/methylene chloride. Elution with 3–10% methanol/methylene chloride gave 0.31 g (66%) of 56 as a white Foam. NMR $^1$H (400 MHz, CDCl$_3$): 7.71(1H, m) 7.29(12H, m), 7.14(6H, m), 7.05(2H, m), 6.55(1H, s), 3.04(2H, m), 2.68(2H, m), 2.51(3H, m), 2.09(2H, m), 1.81(2H, m), 1.58 (2H, ), 1.3(2H, m). MS (LC/MS): 589 (M+).

Step B

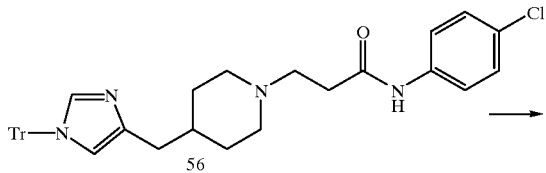

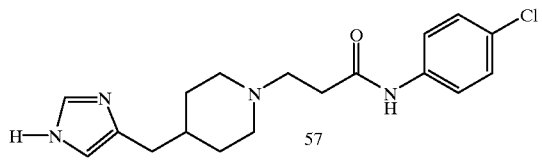

Compound 56 (0.6 g, 1.0 mmol) in methanol (18 ml) and 1N HCl (6 ml) was warmed to 60° C. Progress of the reaction was monitored by quenching a small aliquot of the reaction with 1 N sodium hydroxide and ethyl acetate. TLC (5% ammonia(conc)/10% methanol/85% methylene chloride) indicated consumption of starting material. The mixture was cooled to room temperature and concentrated. The residue was not totally soluble in ether/water. The residue was made basic with 1N NaOH, diluted with methylene chloride, transferred to a separatory funnel and extracted with methylene chloride. The extracts were combined, washed with brine, dried over anhydrous sodium sulfate, filtered and concentrated onto enough silica gel such that a free flowing powder was obtained. The powder was loaded onto a chromatography column prepacked with silica and 10% methanol/methylene chloride. Elution with 10% methanol/methylene chloride followed by 5% ammonia (concentrated)/10% methanol/ chloride) gave the title compound as a clear oil. The oil was redissolved in methylene chloride and treated with an excess of HCl (4M in dioxane) and concentrated in vacuum to give 0.205 g (44%) of 57 as a clear glass. NMR $^1$H (400 CD$_3$OD): 8.85(1H, s), 7.50(2H, d, J=11.4 Hz), 7.40(1H, s), 7.05(2H, d, J=11.4 Hz), 4.251 (2H, s), 4.15(2H, t, J=7.5 Hz), 3.46(2H, d, J=16.2 Hz), 3.35(3H, m), 3.02(2H, t, J=16.2 Hz), 2.95(6H, s), 2.74(2H, d, J=9.0 Hz), 2.25(2H, m), 1.93(2H, d,), 1.60(2H, m). MS (FAB): 357 (M+1).

Example 8

Step A

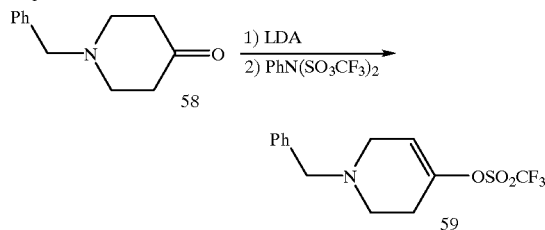

n-butyl lithium (30.4 ml, 48.6 mmol, 1.6M in hexane) was added to a −78° C. solution of diisopropyl amine (6.63 ml, 50.6 mmol) in tetrahydrofuran (75 ml). After 30 minutes 58 (7.5 ml, 40.5 mmol) in tetrahydrofuran (30 ml) was added slowly via cannula. The reaction was stirred at −78° C. for 1.5 hours, then N-phenyltrifluoromethanesulfonamide (15.3 g, 44.5 mmol) in tetrahydrofuran (50 ml) was added via cannula. The mixture was allowed to warm to room temperature overnight. TLC (20% ethyl acetate/hexanes) indicated consumption of starting material. Triethylamine (added to prevent acid hydrolysis of the triflate on silica gel) was added and the resulting mixture was concentrated onto enough silica gel such that a free flowing powder was obtained. The powder was loaded onto a chromatography column prepacked with silica and 20% ethyl acetate/ hexanes. Elution with the same solvent provided 10.8 g (83%) of 59 as a yellow oil. NMR $^1$H (400 MHz, CDCl$_3$): 7.30(5H, m), 5.73(1H, m), 3.63(2H, s), 3.13(2H, dd, J=3.0, 6.4 Hz), 2.72(2H, t, J=5.7 Hz), 2.45(2H, m).

Step B

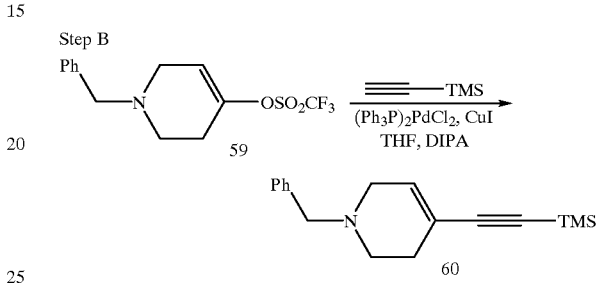

Trimethylsilylacetylene (5.9 ml, 42.1 mmol) was added to a room temperature solution of 59 (10.8 g, 33.7 mmol) in a 3:1 mixture of tetrahydrofuran and diisopropylamine (50 ml). Dichlorobis(triphenylphosphine)palladium (II) (1.42 g, 2.0 mmol) and copper (I) iodide (1.1 g, 5.7 mmol) were added. The color of the reaction progressed from red to brown to black. After 1 hour, TLC (5% ethyl acetate/ hexanes) indicated consumption of starting material. The reaction was diluted with ethyl ether, transferred to a separatory funnel, washed with water, 3/1 saturated ammonium chloride/ammonia (conc) and brine, dried over anhydrous sodium sulfate, filtered and concentrated onto enough silica gel such that a free flowing powder was obtained. The powder was loaded onto a chromatography column prepacked with silica and 10% ethyl acetate/hexanes. Elution with the same solvent provided 6.1 g (67%) of 60 as a yellow solid. NMR $^1$H (400 MHz, CDCl$_3$): 7.35(5H, m), 6.14(1H, m), 3.63(2H, s), 3.08(2H, m), 2.63(2H, t, J=5.7 Hz), 2.33 (2H, m), 0.23(9H, s).

Step C

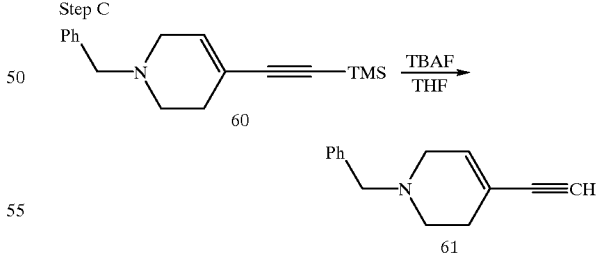

Tetrabutylammonium fluoride (27 ml, 27.0 mmol, 1M in tetrahydrofuran) was added to a room temperature solution of 60 (6.1 g, 22.5 mmol) in tetrahydrofuran (100 ml). After ~2 hours, TLC (20% ethyl acetate/hexanes) indicated consumption of starting material. The reaction mixture was diluted with ethyl acetate, transferred to a separatory funnel, washed with water and brine, dried over anhydrous sodium sulfate, filtered and concentrated onto enough silica gel such that a free flowing powder was obtained. The powder was loaded onto a chromatography column prepacked with silica and 10% ethyl acetate/hexanes. Elution with the same solvent provided 3.4 g (76%) of 61 as a yellow solid. NMR $^1$H (400 MHz, CDCl$_3$): 7.36(5H, m), 6.17(1H, m), 3.65(2H, s), 3.11(2H, m), 2.91(1H, s), 2.64(2H, t, J=5.6 Hz), 2.35(2H, m).

Step D

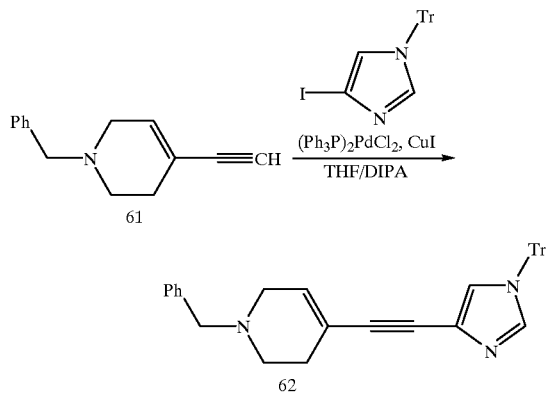

61 (3.42 g, 17.3 mmol) and 1-triphenylmethyl-4-iodoimidazole (6.3 g, 14.4 mmol) were dissolved in tetrahydrofuran (100 ml) and diisopropylamine (40 ml). Dichlorobis(triphenylphosphine)palladium (II) (1.22 g, 1.7 mmol) and copper (I) iodide (0.4 g, 1.7 mmol) were added. The reaction mixture was allowed to stir at room temperature overnight. TLC (5% methanol/methylene chloride) indicated consumption of starting material. The reaction was diluted with methylene chloride, transferred to a separatory funnel, washed with water, 3/1 saturated ammonium chloride/ammonia (conc) and brine, dried over anhydrous sodium sulfate, filtered and concentrated. The residue was recrystallized form ethyl acetate to give 7.02 g (98%) of 62 as a slightly yellow solid. NMR $^1$H (400 MHz, CDCl$_3$): 7.44(1H, d, J=1.1 Hz), 7.40(14H, m), 7.18(6H, m), 7.06(1H, d, J=1.5 Hz), 6.12(1H, m), 3.64(2H, s), 3.12(2H, m), 2.64 (2H, t, J=5.7 Hz), 2.39(2H, m). MS(FAB): 505 (M+).

Step E

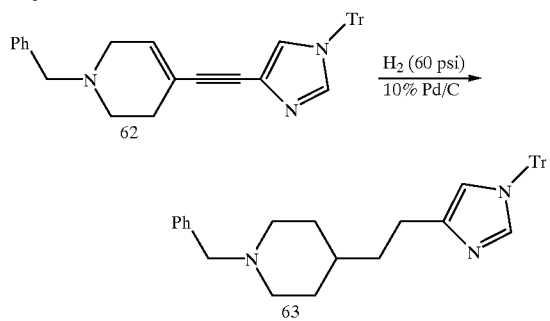

62 (7.0 g, 14.1 mmol) was dissolved in a mixture of tetrahydrofuran (250 ml), methanol (200 ml) and methylene chloride (100 ml) and purged with nitrogen. 10% palladium on carbon (1.0 g) was added and the resulting suspension was hydrogenated on a Parr apparatus overnight at 60 psi. TLC (5% methanol/methylene chloride) indicated a considerable amount of remaining starting material. The mixture was filtered through celite, fresh 10% palladium on carbon was added and the mixture was again hydrogenated on a Parr apparatus at 60 psi for two days TLC (5% methanol/methylene chloride) indicated a considerable amount of remaining starting material. 20% palladium hydroxide on carbon (1.0 g) and acetic acid (60 ml) were added and the mixture was again hydrogenated on a Parr apparatus at 60 psi overnight. The mixture was filtered and concentrated. TLC (5% ammonia (conc)/10% methanol/methylene chloride) indicated a number of new spots. The residue was redissolved in acetic acid (75 ml) and 20% palladium hydroxide on carbon (1.0 g) was added and the mixture was hydrogenated at 50 psi for two days. The reaction was filtered through celite, the filter cake was well washed with methanol. The filtrate was concentrated and the residue was azeotroped with toluene (3X) to remove residual acetic acid. The residue was dissolved with 1N NaOH and methylene chloride, transferred to a separatory funnel and extracted with methylene chloride. The extracts were combined, washed with water and brine, dried over anhydrous sodium sulfate and concentrated to provide 6.8 g of an amber oil. Chromatography on silica eluting with 4% ammonia(conc)/10% methanol/86% methylene chloride provided 0.7 g (10%) of 63. NMR $^1$H (400 MHz, CD$_3$Cl$_3$): 7.29(15H, m), 7.13(6H, m), 6.49(1H, s), 3.58(2H, m), 2.94(2H, m), 2.54 (2H, t, J=8.0 Hz), 1.98(2H), 1.66(2H, m), 1.54(3H, m), 1.29(2H).

Step F

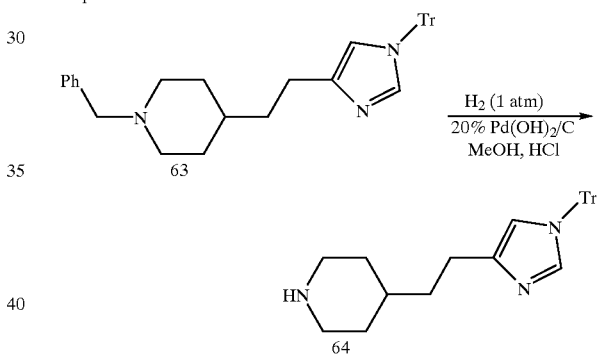

63 (0.019 g, 0.054 mmol) was dissolved in methanol (1 ml), 1M HCl (2 drops) was added. The resulting solution was purged with nitrogen. 10% palladium on carbon (0.005 g) was added and the mixture was stirred under a balloon of hydrogen gas overnight. The mixture was filtered through celite, the filter cake was well washed with methanol and concentrated to give 0.0128 g of a clear oil. $^1$H NMR analysis indicated no reaction had occurred. The oil was redissolved in methanol (1 ml), HCl (1 drop) was added. The resulting solution was purged with nitrogen. 20% palladium hydroxide on carbon (0.01 g) was added and the mixture was stirred under a balloon of hydrogen gas overnight. The mixture was filtered through celite, the filter cake was well washed with methanol and concentrated to give 0.0085 g of 64 as a clear oil. NMR $^1$H (400 MHz, CD$_3$OD): 8.87(1H, s), 7.41(1H, s), 3.45(2H, m), 3.04(2H, m), 2.85(2H, m), 2.05 (2H, m), 1.75(3H, m), 1.53(3H, m).

Compound (64) was then used to produce compounds of formula I, e.g. by following the procedures of the examples above.

Example 9

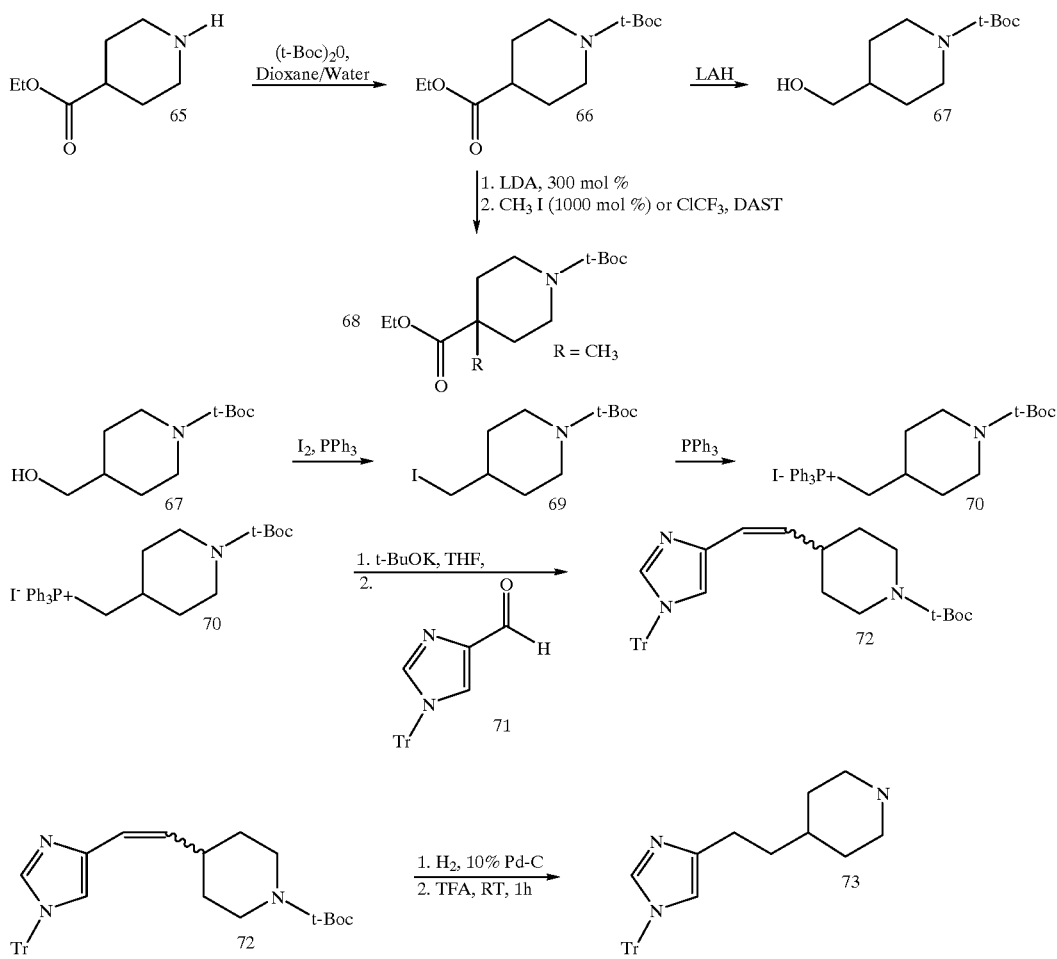

Commercially available ethyl isonipecotate was protected with di-tert-butyl dicarbonate, the ethyl ester reduced with lithium aluminum hydride and the intermediate alcohol was transformed into the desired iodide 69 with iodine according to the procedure described by A. Villalobos in the Journal of Medicinal Chemistry 1994, 37, 2721–2734.

A 500 mL round bottomed flask was charged with iodide 69 (10.0 g, 30.75 mmol), triphenylphosphine (16.9 g, 64.6 mmol) and 150 mL acetonitrile.

The solution was heated at reflux for 16 h, cooled to room temperature and then concentrated in vacuo to a yellow oil. The crude product was further purified by chromatography on silica using a gradient from 4:1 hexane: ethyl acetate to 100% ethyl acetate and final elution with 95:5 methylene chloride: methanol to afford phosphonium salt 70 (7.13 g) in 40% yield.

A 500 mL round bottomed flask was charged with phosphonium salt 70 (7.13 g, 12.14 mmol), n-trityl imidazole-4-carboxaldehyde (4.5 g, 13.14 mmol) and 250 mL dry tetrahydrofuran an the reaction mixture was cooled to 4° C. Potassium t-Butoxide (14 ml of a 1 M in Dioxane, 14 mmol) was added dropwise and the solution was allowed to warm slowly to room temperature and the disappearance of aldehyde was monitored by TLC. Additional potassium t-butoxide was added at 4 h (2.4 mL, 2.4 mmol) and the reaction was allowed to stir at room temperature. After a total of 16 h the reaction was filtered and the filtrate was concentrated to an oil. Elution on silica gel column with hexanes: ethyl acetate afforded pure alkene 72 (3.2 g) in 51% yield as a mixture of E/Z isomers.

A 500 mL round bottomed flask was charged with alkene 72 (3.2 g), $PtO_2$ (0.75 g), and 150 mL methanol and affixed with a three-way stopper with a hydrogen bladder. The heterogeneous reaction was stirred under hydrogen for 2 h. The catalyst was filtered and the filtrate was concentrated to an oil (3.2 g). The crude intermediate was redissolved in 180 mL dioxane and treated at room temperature with 1M TFA in dioxane (20 mL, 20 mmol) for 24 h. The pH of the reaction mixture was adjusted to greater than 8 with sodium hydroxide (1M), ethyl acetate was added and the layers were separated. The organic layer was washed with brine, dried over magnesium sulfate and concentrated to a semi-solid. The crude product was purified by chromatography (methylene chloride: methanol eluent) to afford pure 73 (1.8 g, 69% yield).

Example 10

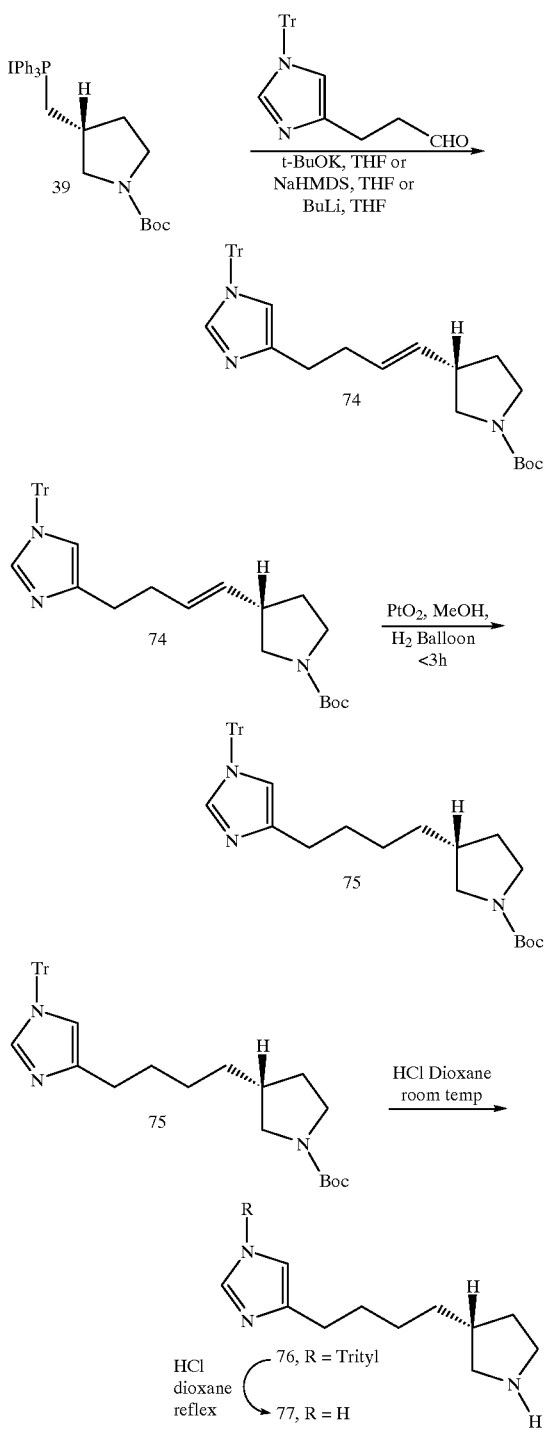

To a flask containing the phosphonium salt 39 (3.5 g, 6.11 mmol) was added dry THF (30 mL) under a nitrogen atmosphere. The mixture was cooled to 0° C. and t-BuOK was added (1.0M solution, 8 g, 8 mmols) dropwise via syringe. The resulting yellow mixture was stirred for 20 min, then the 3-carbon aldehyde (2.4 g, 6.55 mmol) was added in 8 mL THF via syringe. The reaction mixture was stirred for 24 h at 25° C. then quenched by the addition of $NH_4Cl$ solution. The aqueous portion was extracted with EtOAc. The combined organics were washed with brine, dried over MgSO4, filtered and concentrated. Chromatogrphy on silica gel (40% EtOAc-hexane→60% EtOAc) afforded 74 2.6 g (71%) of material. MS (electrosrpay, M+H)=534.

To Compound 74 (2.3 g, 4.3 mmol) dissolved in MeOH was added $PtO_2$ (0.4 g). A hydrogen balloon was placed over the reaction mixture, and stirring was continued for 2–3 h at 25° C. The reaction mixture was then chromatographed on $SiO_2$ (100% hexane increasing to 75% EtOAc-hexane) to remove the catalyst and obtain the pure product 75, 2.24 g (97%). MS (electrosrpay, M+H)=536.

To a dioxane solution of compound 75 (2.0 g, 3.7 mmol) was added a 4M HCl-dioxane solution (10 mL) at 25° C. The mixture was stirred for about 6 h, then cooled to 0° C., and 5% NaOH was added to bring the pH to 7. The mixture was extracted with EtOAc, and the combined organics were washed with brine, dried over $MgSO_4$, filtered and concentrated, to give 1.14 g (100%) of compound 76. MS (electrosrpay, M+H)=436.

Treatment of 76 (200 mg, 0.46 mmol) again with 4M HCl-dioxane (5 mL) at 80° C. for 4 h affords 140 mg of compound 77. MS (Cl, M+H)=194.

The compounds below were prepared following procedures similar to those described above.

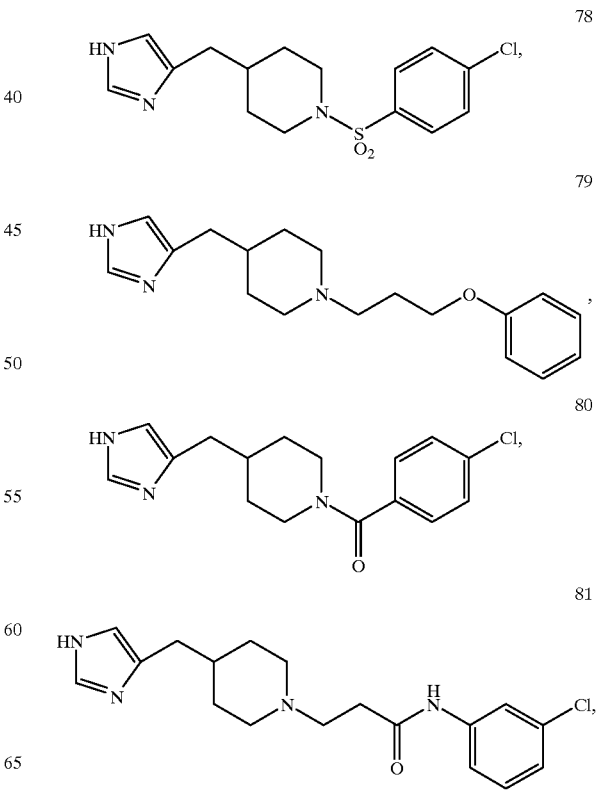

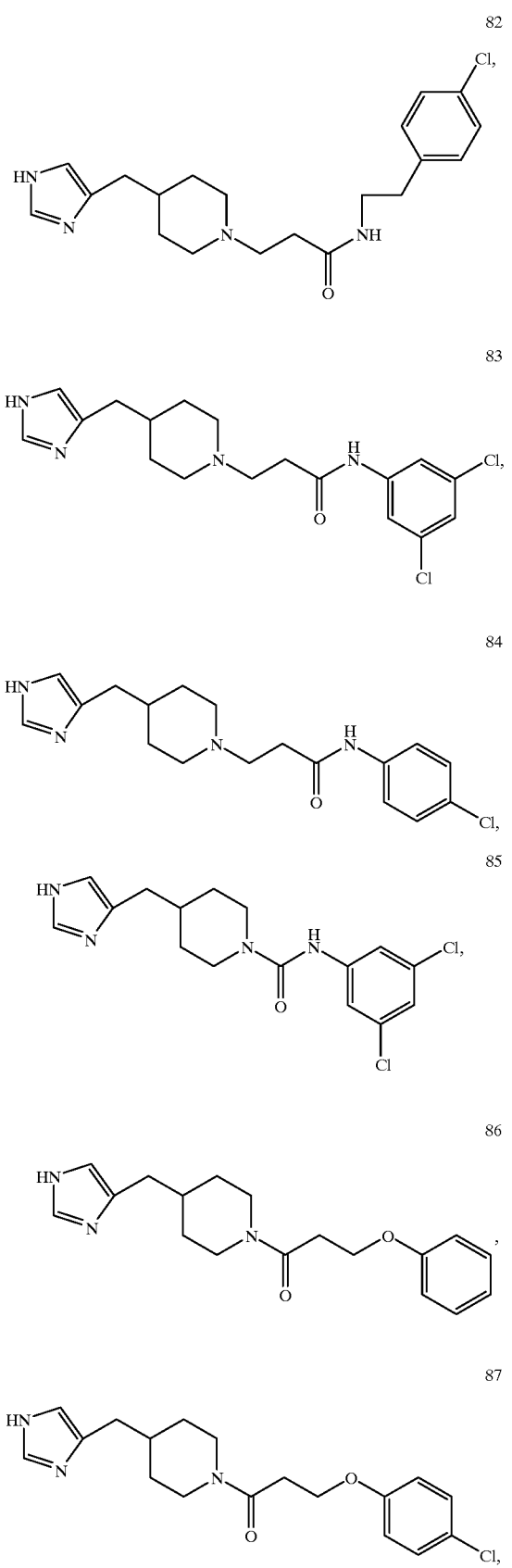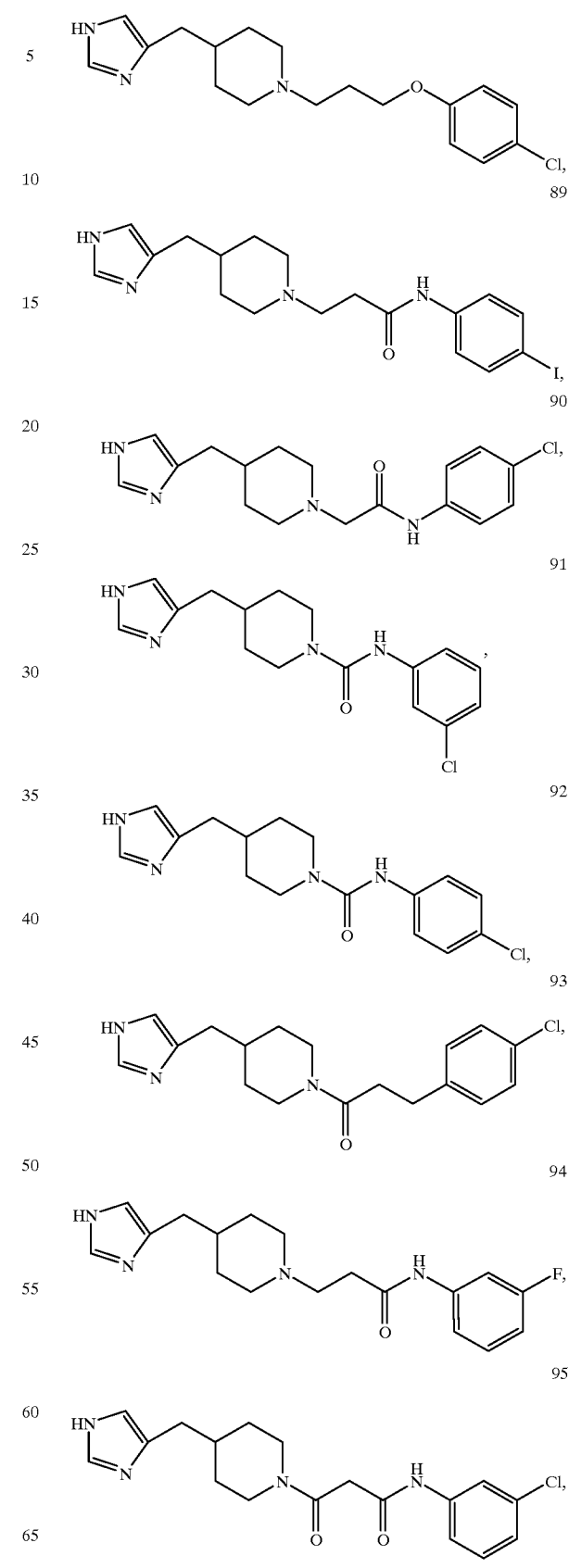

96
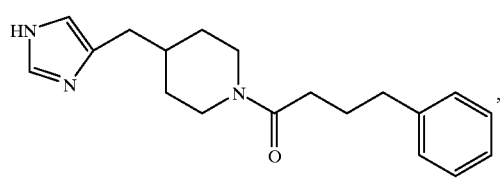
97
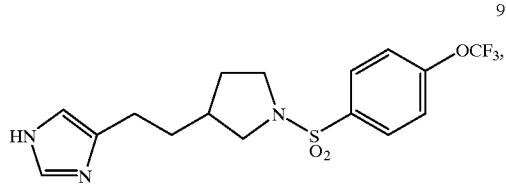
98
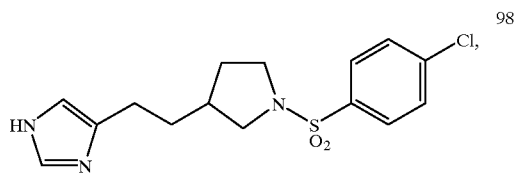
99
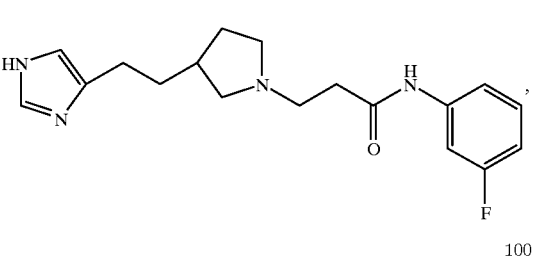
100
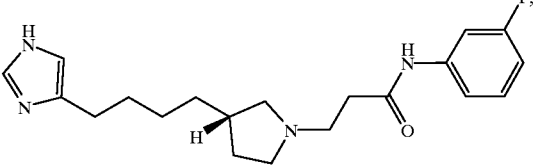
101
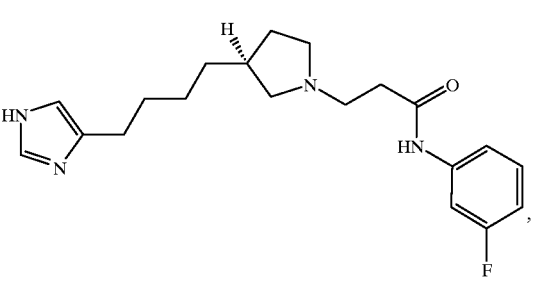
102
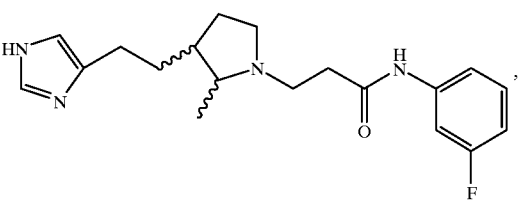
103
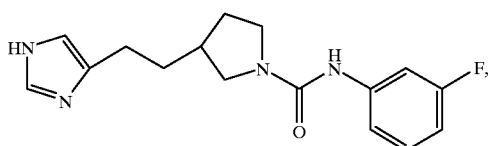
104
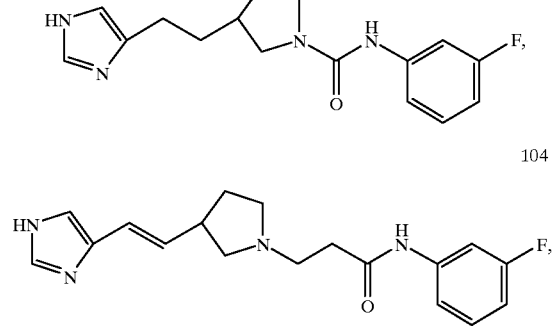
105
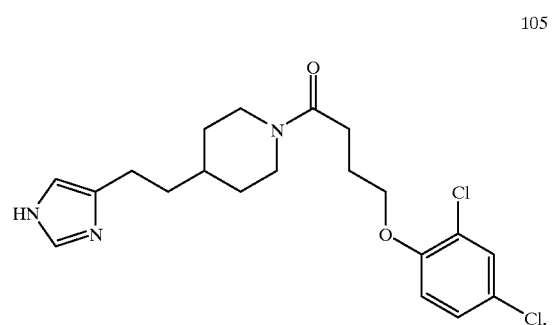
106
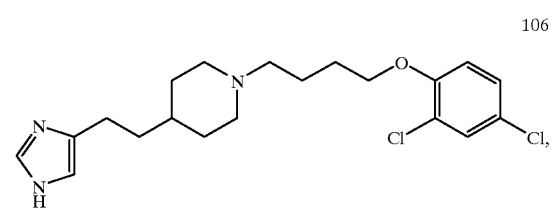
107
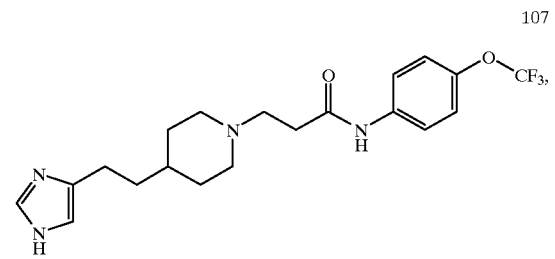
108
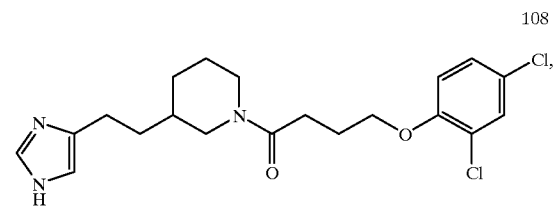
109
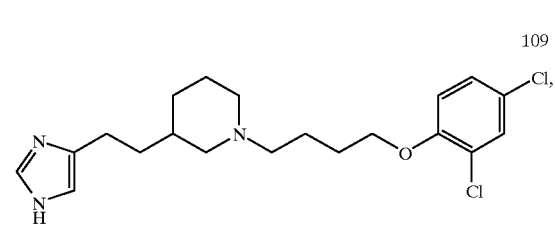

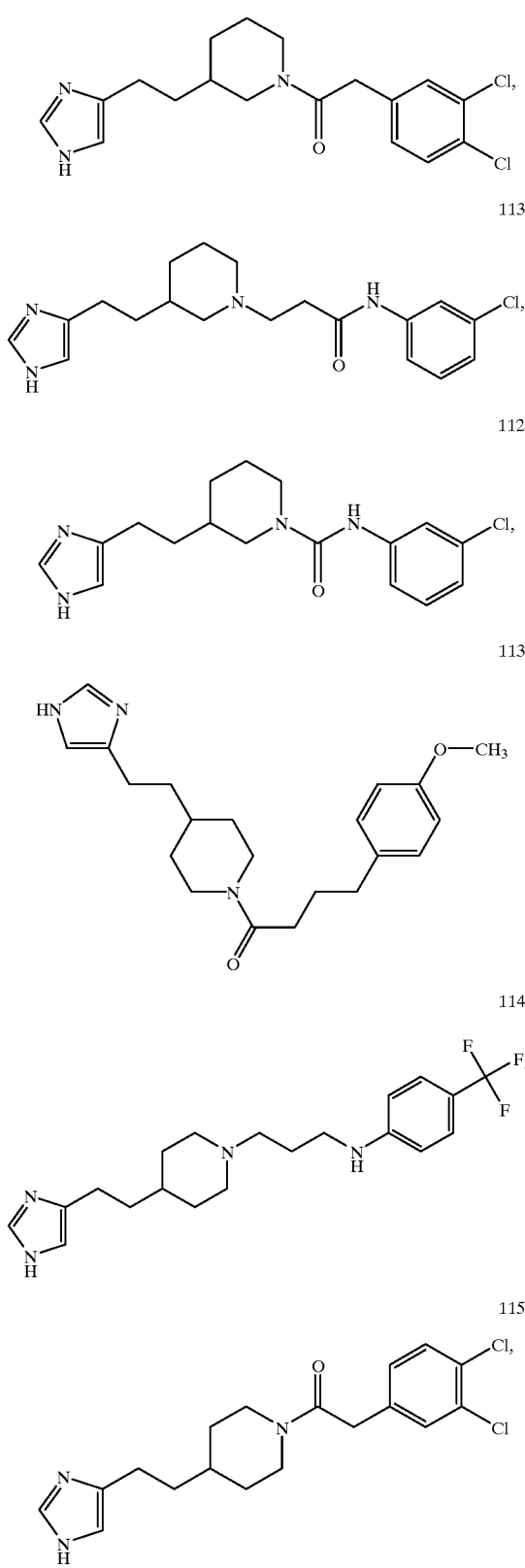
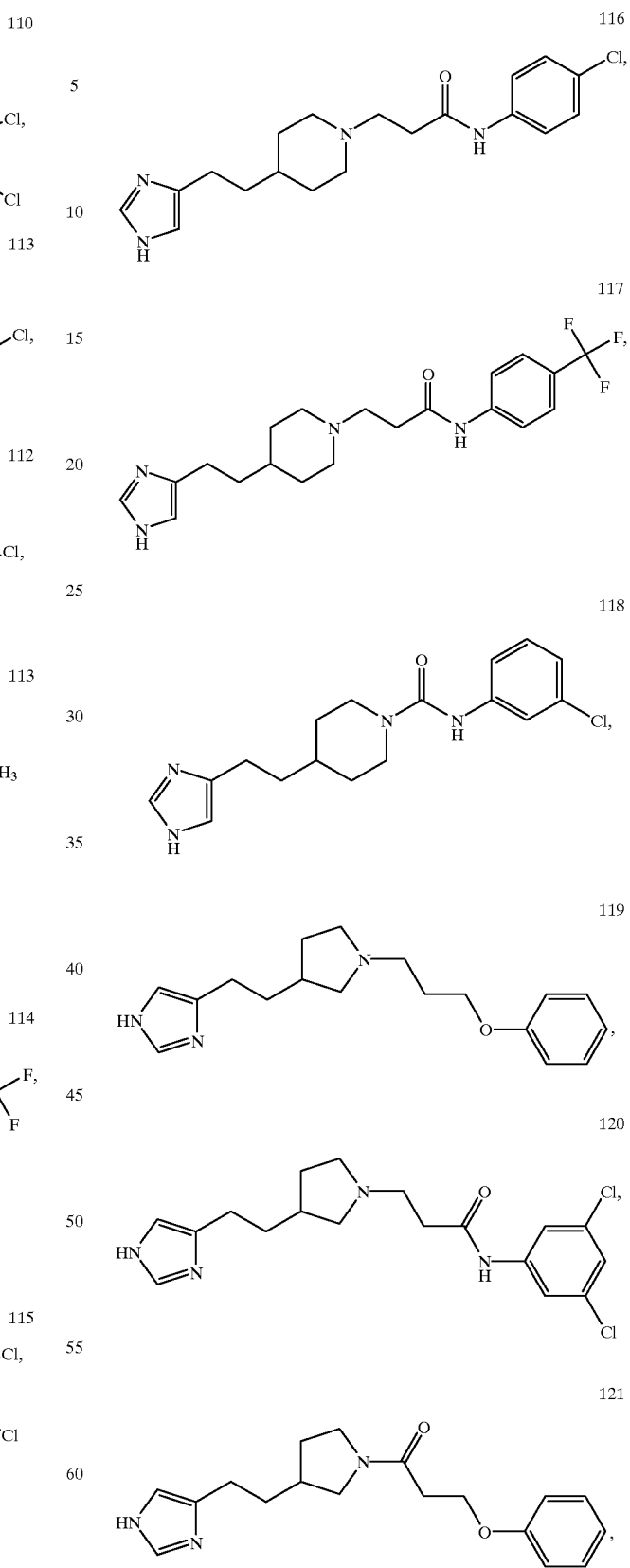

-continued

122

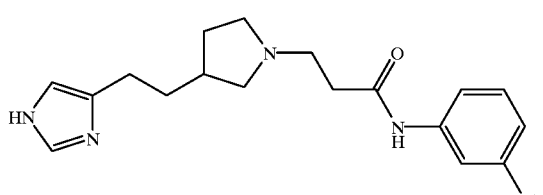

and

123

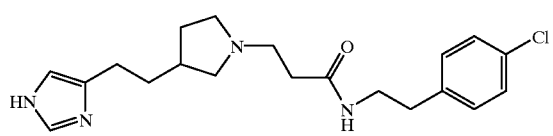

MASS SPECTROMETRY DATA

| COMPOUND NO. | MASS SPEC | COMPOUND NO. | MASS SPEC |
|---|---|---|---|
| 78 | (CI) 340 (M + 1) | 79 | (FAB) 300 (M + 1) |
| 80 | (CI) 304 (M + 1) | 81 | (EI) 346 (M+) |
| 82 | (EI) 374 (M+) | 83 | (EI) 380 (M+) |
| 84 | (CI) 347 (M + 1) | 85 | (CI) 353 (M + 1) |
| 86 | (EI) 313 (M+) | 87 | (EI) 347 (M+) |
| 88 | (EI) 333 (M+) | 89 | (CI) 439 (M + 1) |
| 90 | (FAB) 333 (M + 1) | 91 | (FAB) 319 (M + 1) |
| 92 | (FAB) 319 (M + 1) | 93 | (FAB) 332 (M + 1) |
| 94 | (FAB) 331 (M + 1) | 95 | (FAB) 361 (M + 1) |
| 96 | (FAB) 312 (M + 1) | 97 | (CI) 390 (M + 1) |
| 98 | (CI) 340 (M + 1) | 99 | (CI) 331 (M + 1) |
| 100 | (CI) 359 (M + 1) | 101 | Electrospray 359 (M + 1) |
| 102 | Electrospray 345 (M + 1) | 103 | FAB 303 (M + 1) |
| 104 | (CI) 329 (M + 1) | 105 | High Resolution Calc. 410.1402 Found 410.1410 |
| 106 | High Resolution Calc. 396.1609 Found 396.1618 | — | — |

The compounds of this invention are either agonists or antagonists of the histamine $H_3$ receptor. The binding affinity of the compounds of the invention to the $H_3$ receptor may be demonstrated by the procedure described below:

$H_3$ Receptor Binding Assay

The source of the $H_3$ receptors in this experiment was guinea pig brain. The animals used weighed 400–600 g. The tissue was homogenized using a Polytron in a solution of 50 mM Tris, pH 7.5. The final concentration of tissue in the homogenization buffer was 10% w/v. The homogenates were centrifuged at 1000×g for 10 min. in order to remove clumps of tissue and debris. The resulting supernatants were then centrifuged at 50,000×g for 20 min. in order to sediment the membranes, which were next washed 3 times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 µg/ml with 0.1% DMSO. Membranes were then added (400 µg of protein) to the reaction tubes. The reaction was started by the addition of 3 nM [$^3$H]R-α-methylhistamine (8.8 Ci/mmol) or [$^3$H]-N-methylhistamine (80 Ci/mmol) and incubated at 30° for 30 min. Bound ligand was separated from unbound ligand by filtration, and the amount of radioactive ligand bound to the membranes was quantitated by liquid scintillation spectrometry. All incubations were performed in duplicate and the standard error was less than 10% in all instances. Compounds that inhibited greater than 70% of the specific binding of radioactive ligand to the receptor were serially diluted to determine a $K_i$ (nM). The results are given in the table below Biological Data

| Compound # | $K_i$ (nM) | Compound # | $K_i$ (nM) |
|---|---|---|---|
| 45 | 0.9 | 78 | 150 |
| 79 | 4 | 81 | 0.2 |
| 82 | 0.7 | 83 | 0.7 |
| 84 | 0.4 | 85 | 220 |
| 86 | 5 | 87 | 9 |
| 88 | 9 | 89 | 5 |
| 90 | 90 | 91 | 20 |
| 92 | 160 | 93 | 40 |
| 94 | 0.1 | 95 | 50 |
| 96 | 8 | 97 | 58 |
| 113 | 67 | 114 | 60 |
| 115 | 57 | 116 | 11 |
| 117 | 50 | 118 | 210 |

Compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg to 500 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day it desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 1 mg to 2000 mg/day preferably 10 to 1000 mg/day, in one to four divided doses to achieve relief of the symptoms. The compounds are non-toxic when administered within this dosage range.

The following are examples of pharmaceutical dosage forms which contain a compound of the invention. As used therein, the term "active compound" is used to designate one of the compounds of the formula I or salt thereof. The scope of the invention in its pharmaceutical composition aspect is not to be limited by the examples provided.

Pharmaceutical Dosage Form Examples

Example A

| | Tablets | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1-3 minutes. Compress the mixture to appropriate size and weigh on a suitable tablet machine.

Example B

| | Capsules | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

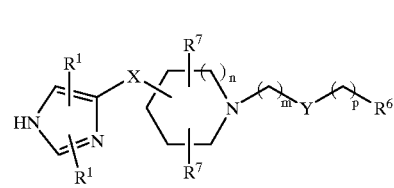

(I)

or pharmaceutically acceptable salts or solvates thereof, wherein:

X is a straight chain alkyl group having 1 to 7 carbon atoms or an alkene or alkyne group with 2 to 4 carbon atoms; wherein said alkyl or alkene groups are optionally substituted with up to two $R^7$ groups;

n is 0, 1 or 2 m is 2 to 4;

p is 0 to 4;

Y represents —$SO_2$—; —CS—; —CO—; —$CONR^5$—; —$CO(CH_2)_wO$— (with w being 1 to 4); —COO—; —$CON(OR^5)$—; —$C(NR^5)NR^5$—; —$SO_2NR^5$— or —$CSNR^5$—; —$CHOR^5$—; —$NR^5CONR^5$—; —$NR^5CO$—; —$NR^5$—; —$OCONR^5$—; —$NR^5C(NR^5)NR^5$—; —$NR^5CSNR^5$; —$NR^5CS$—; —$NR^5SO_2$—; —$NR^5C(O)O$—; or —$CSNR^5$—;

each $R^5$ independently represents hydrogen, alkyl or benzyl;

$R^6$ is selected from:
(1) aryl,
(2) heteroaryl,
(3) substituted aryl having 1–3 substituents independently selected from of alkyl, halogen, trihalomethyl, CN, $NO_2$, $OR^{10}$ or $NR^{10}R^{11}$, wherein $R^{10}$ and $R^{11}$ are independently selected from H, alkyl or trihalomethyl,
(4) substituted heteroaryl having 1–3 substituents independently selected from alkyl, halogen, trihalomethyl, CN, $NO_2$, $OR^{10}$ or $NR^{10}R^{11}$, wherein $R^{10}$ and $R^{11}$ are as defined above; or (5) substituted heterocyclic having 1–3 substituents independently selected from alkyl trihalomethyl or $NR^{10}R^{11}$, wherein $R^{10}$ and $R^{11}$ as defined above, said substituents being bound to carbon atoms in the ring such that the total number of substituents in the ring is 1 to 3; and wherein the heterocyclic ring contains substitutable nitrogen atoms, said nitrogen atoms are optionally substituted with lower alkyl;

when Y is —$SO_2$—, then $R^6$, in addition to the above groups, also represents alkyl having 1 to 7 carbon atoms or a group —$NR^{10}R^{11}$ wherein $R^{10}$ and $R^{11}$ are as defined above;

each $R^1$ is independently selected from hydrogen, alkyl or trihalomethyl;

each $R^7$ is independently selected from hydrogen, alkyl, trihalomethyl, phenyl or benzyl, wherein said phenyl and benzyl are optionally substituted by one to three substituents independently selected from of alkyl, halogen, trihalomethyl, CN, $NO_2$, $OR^{10}$ or $NR^{10}R^{11}$, wherein $R^{10}$ and $R^{11}$ wherein $R^{10}$ and $R^{11}$ as above defined.

2. The compound of claim 1 having the formula

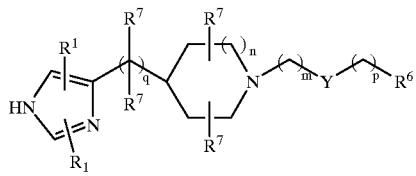

wherein:
q is 1 to 7;
m is 2 to 4;
n is 0 or 1;
p is 0 to 4; and
Y represents —$SO_2$—, —$SO_2NH$—, —CONH—, —CO—, —C(NH)NH—, or —$CO(CH_2)_wO$—, —NHCONH—, —O— or —NHC(NH)NH—.

3. The compound of claim 2 wherein $R^6$ is phenyl or substituted phenyl.

4. The compound of claim 2 wherein n is 1; Y is selected from —$SO_2$—, —CONH—, —CO—, or —$CO(CH_2)_wO$—, —NHCONH— or —O—.

5. A compound selected from:

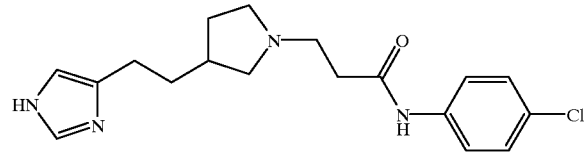

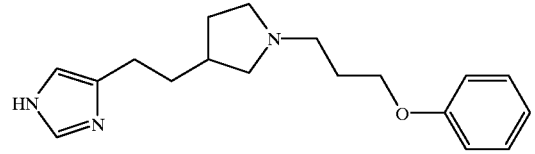

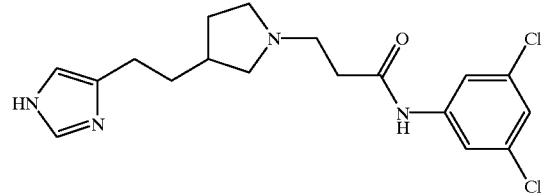

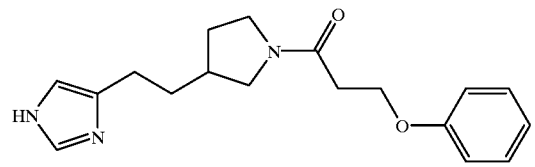

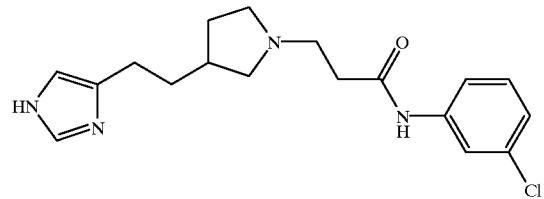

-continued
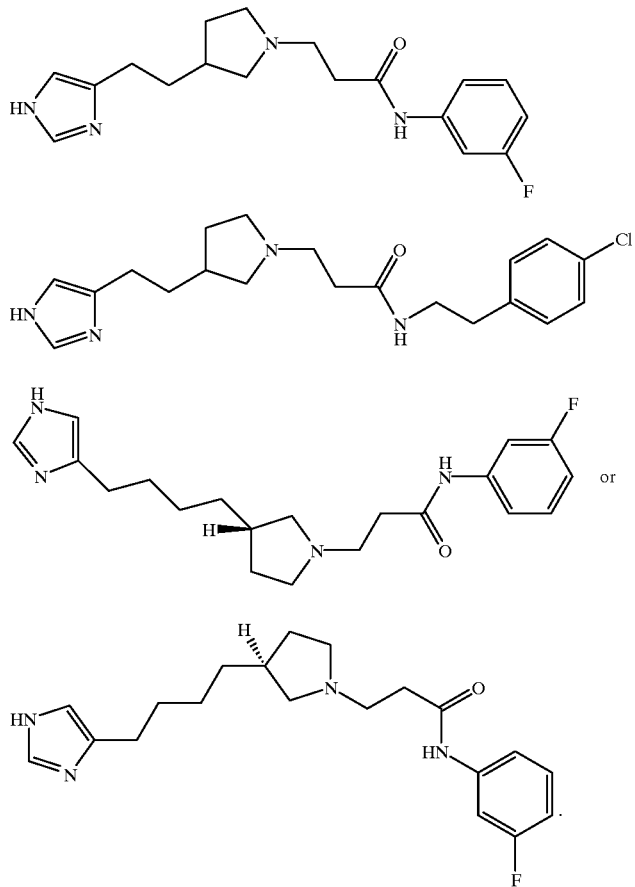
6. A compound selected from:
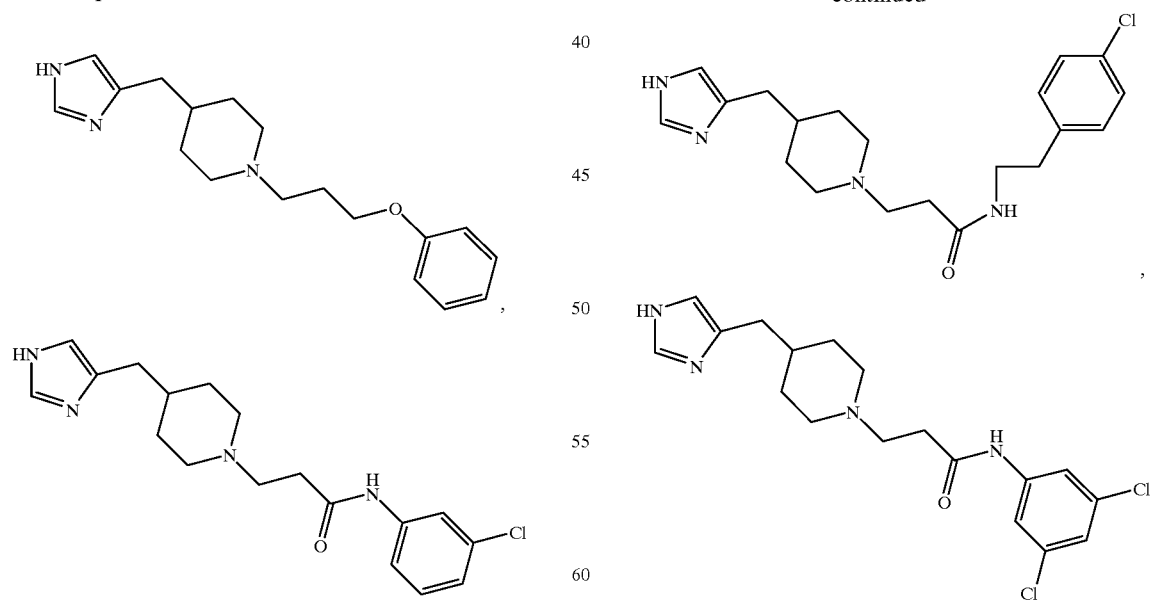

-continued

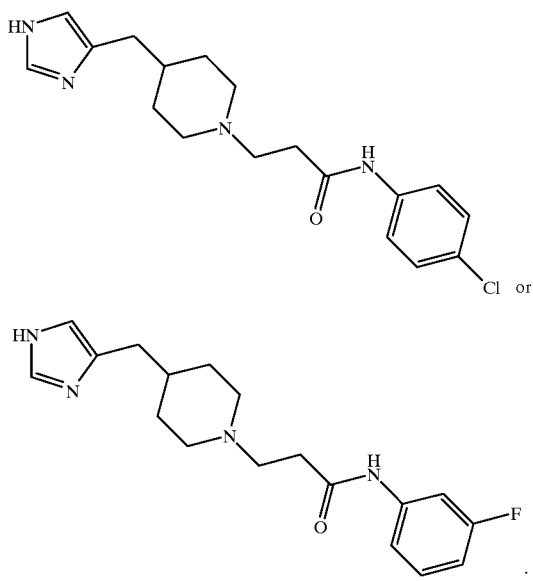

7. A pharmaceutical composition comprising a pharmaceutically acceptable carrier and a therapeutically effective amount of a compound, or a salt or solvate thereof, of claim 1.

8. A method for treatment of upper airway allergic responses comprising administering a combination of a histamine $H_3$ receptor antagonistic effective amount of a compound, or a salt or solvate thereof, of claim 1 with a histamine $H_1$ receptor antagonist.

9. The method of claim 8 wherein said $H_1$ antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

10. The method of claim 9 wherein said $H_1$ antagonist is selected from: loratadine, descarboethoxyloratadine, fexofenadine, cetirizine.

11. The method of claim 10 wherein said $H_1$ antagonist is selected from: loratadine or descarboethoxyloratadine.

12. A compound selected from:

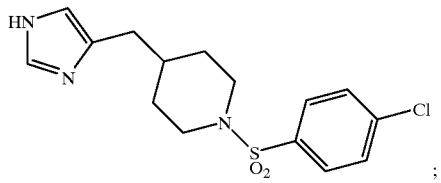
78

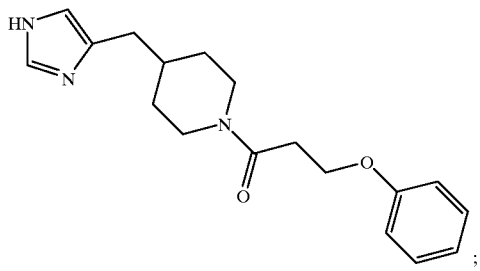
86

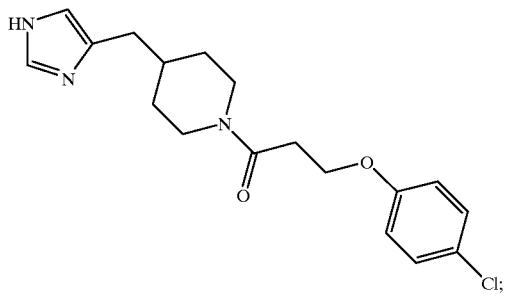
87

88
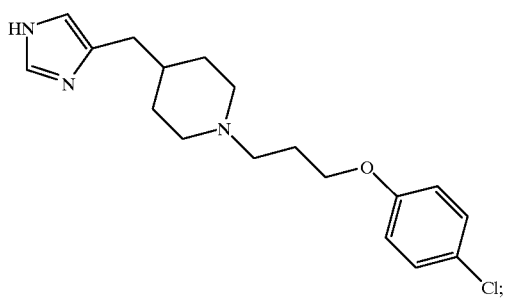
89
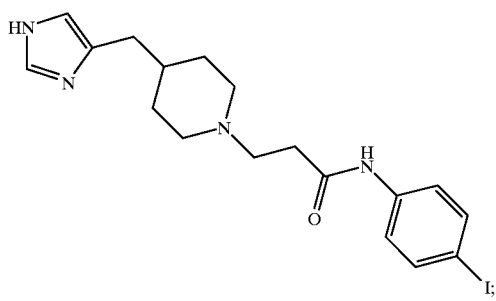
90
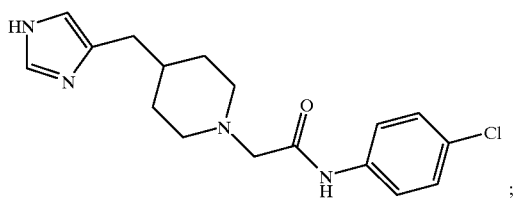
95
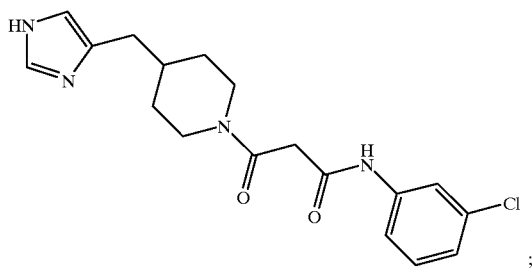
97
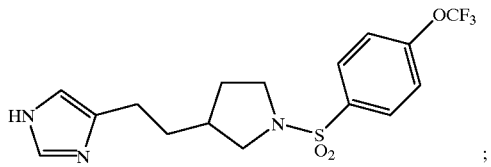
98
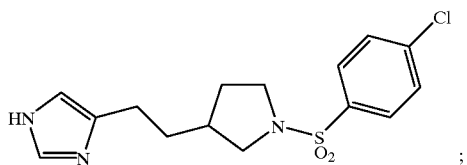

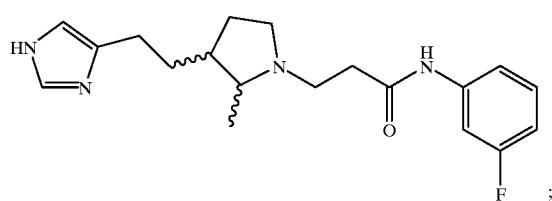
102
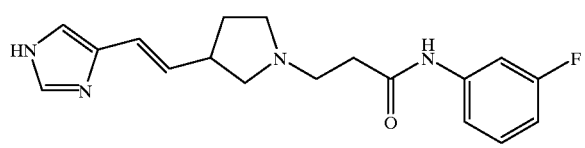
104
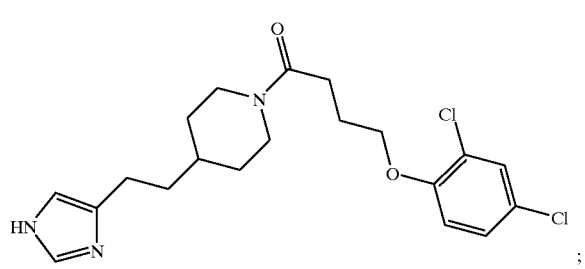
105
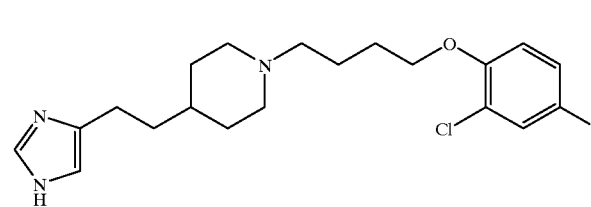
106
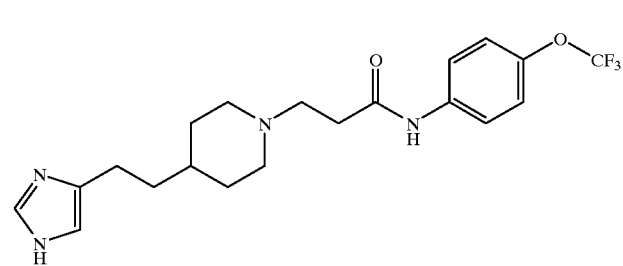
107
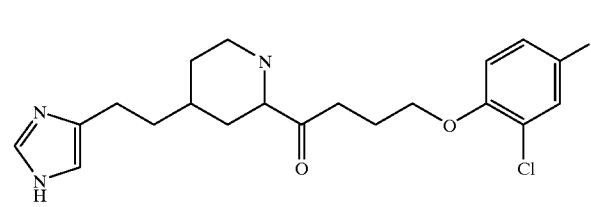
108
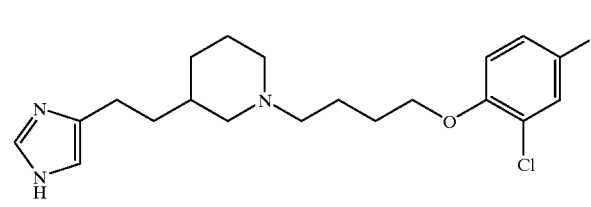
109

-continued

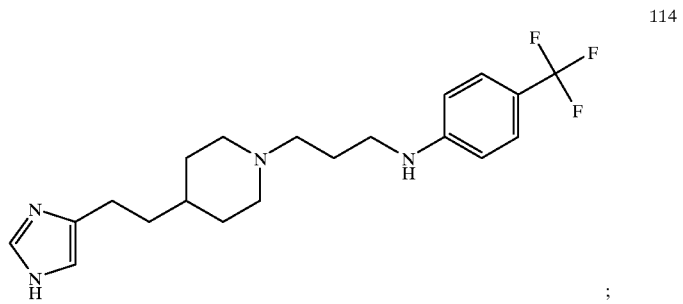

114

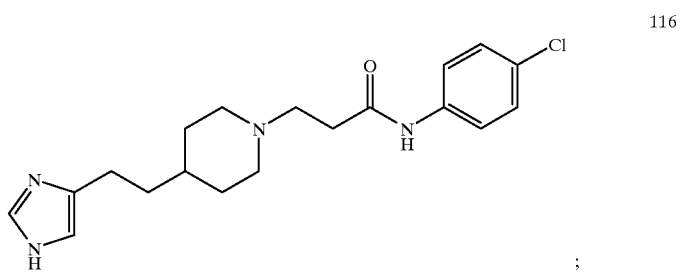

116

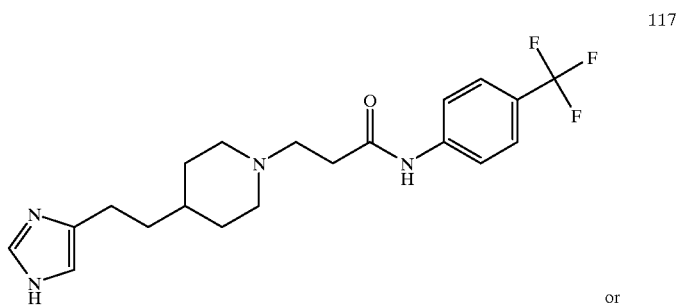

117 or

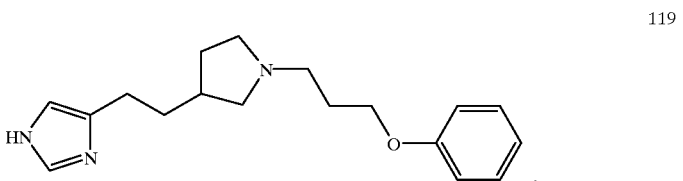

119

13. A pharmaceutical composition comprising a pharmaceutically acceptable carrier and a therapeutically effective amount of a compound, or a salt or solvate thereof, of claim 12.

14. A method for treatment of upper airway allergic responses comprising administering a combination of a histamine $H_3$ receptor antagonistic effective amount of a compound, or a salt or solvate thereof, of claim 12 with a histamine $H_1$ receptor antagonist.

15. The method of claim 14 wherein said $H_1$ antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

16. The method of claim 15 wherein said $H_1$ antagonist is selected from: loratadine, descarboethoxyloratadine, fexofenadine, cetirizine.

17. The method of claim 16 wherein said $H_1$ antagonist is selected from: loratadine or descarboethoxyloratadine.

18. A compound selected from:
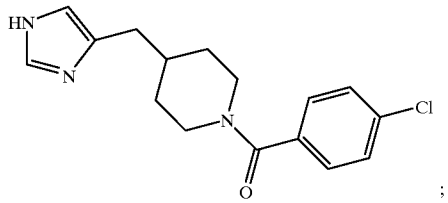
80
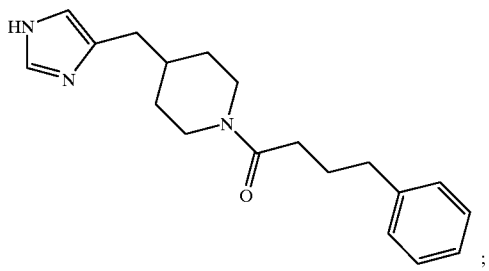
85
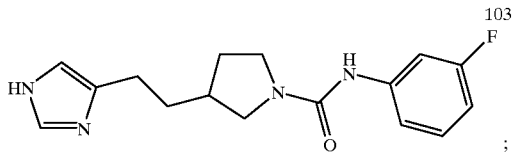
91
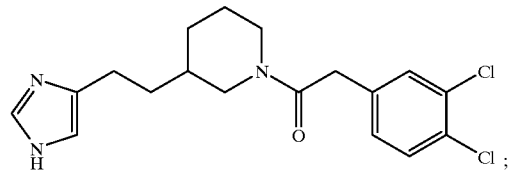
92
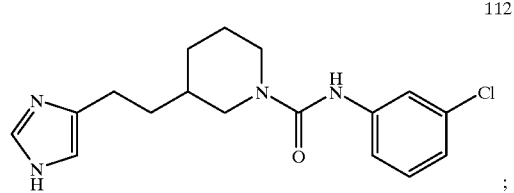
93
-continued
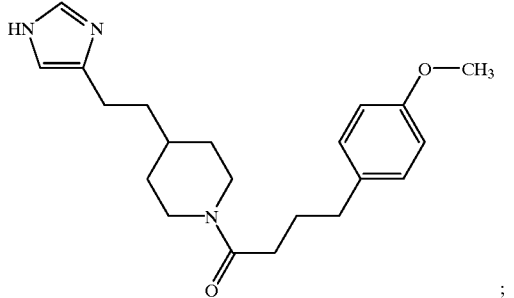
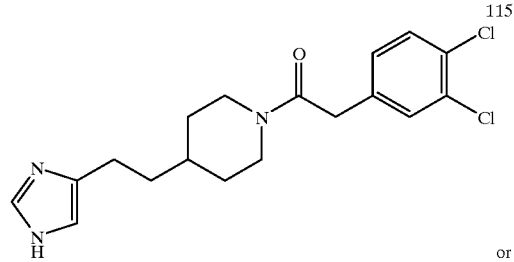
or -continued

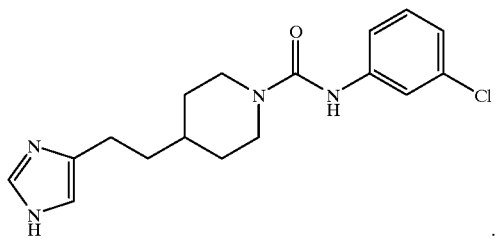

118

19. A pharmaceutical composition comprising a pharmaceutically acceptable carrier and a therapeutically effective amount of a compound, or a salt or solvate thereof, of claim 18.

20. A method for treatment of upper airway allergic responses comprising administering a combination of a histamine $H_3$ receptor antagonistic effective amount of a compound, or a salt or solvate thereof, of claim 19 with a histamine $H_1$ receptor antagonist.

21. The method of claim 20 wherein said $H_1$ antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

22. The method of claim 21 wherein said $H_1$ antagonist is selected from: loratadine, descarboethoxyloratadine, fexofenadine, cetirizine.

23. The method of claim 22 wherein said $H_1$ antagonist is selected from: loratadine or descarboethoxyloratadine.

* * * * *